United States Patent
Thompson et al.

(10) Patent No.: US 10,941,111 B2
(45) Date of Patent: Mar. 9, 2021

(54) ON-DEMAND RAPID SYNTHESIS OF LOMUSTINE UNDER CONTINUOUS FLOW CONDITIONS

(71) Applicant: Purdue Research Foundation, West Lafayette, IN (US)

(72) Inventors: David H Thompson, West Lafayette, IN (US); Robert Graham Cooks, West Lafayette, IN (US); Christina Ramires Ferreira, West Lafayette, IN (US); Zinia Jaman, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/654,103

(22) Filed: Oct. 16, 2019

(65) Prior Publication Data
US 2020/0115330 A1 Apr. 16, 2020

Related U.S. Application Data

(60) Provisional application No. 62/746,045, filed on Oct. 16, 2018.

(51) Int. Cl.
| | | |
|---|---|---|
| *C07C 273/18* | (2006.01) | |
| *B01J 19/00* | (2006.01) | |
| *C07C 275/68* | (2006.01) | |

(52) U.S. Cl.
CPC ..... *C07C 273/1818* (2013.01); *B01J 19/0046* (2013.01); *C07C 273/1854* (2013.01); *B01J 2219/00033* (2013.01); *B01J 2219/00058* (2013.01); *B01J 2219/00279* (2013.01); *C07C 275/68* (2013.01)

(58) Field of Classification Search
None
See application file for complete search history.

(56) References Cited

U.S. PATENT DOCUMENTS

| | | | | |
|---|---|---|---|---|
| 4,182,757 A | * | 1/1980 | Tsujihara | C07H 13/12 514/25 |
| 2012/0142722 A1 | * | 6/2012 | Ziv | A61P 35/00 514/283 |
| 2020/0020516 A1 | * | 1/2020 | Cooks | H01J 49/0463 |

OTHER PUBLICATIONS

Johnston ("The Synthesis of Potential Anticancer Agents. XXXVI. N-Nitrosoureas. II. Haloalkyl Derivatives" J. Med. Chem, 1966, 9(6), p. 892-911) (Year: 1966).*
Chakkath, T., et al. "Alkylation and Carbamylation Effects of Lomustine and Its Major Metabolites and MGMT Expression in Canine Cells." Veterinary Sciences, (2015), 52-68, 2.2.
Dirikolu, L., et al. "Synthesis of Trans- and Cis-4'-Hydroxylomustine and Development of Validated Analytical Method for Lomustine and Trans- and Cis-4'-Hydroxylomustine in Canine Plasma." Journal of Analytical Toxicology, (2009), 595-603, 33.9, Oxford University Press.

(Continued)

*Primary Examiner* — Amy C Bonaparte
(74) *Attorney, Agent, or Firm* — D'Hue Law LLC; Cedric A. D'Hue

(57) ABSTRACT

Disclosed herein is a continuous manufacturing process for lomustine that has a short residence time and 63 percent yield. Major advantages of this process are that the total production cost for lomustine is lower, the product is higher quality, and the manufacturing operation is safer for production personnel.

20 Claims, 27 Drawing Sheets

(56) References Cited

OTHER PUBLICATIONS

Lown, J. W. et al. "Synthesis of Specifically Nitrogen-15- and Carbon-13-Labeled Antitumor (2-Haloethyl) Nitrosoureas.The Study of Their Conformations in Solution by Nitrogen-15 and Carbon-13 Nuclear Magnetic Resonance Electronic Control in Their Aqueous Decomposition." Journal of Organic Chemistry, (1981), 5309-5321, 46.26, American Chemical Society.
Kaina, B., et al. "MGMT: Key Node in the Battle against Genotoxicity, Carcinogenicity and Apoptosis Induced by Alkylating Agents." DNA Repair, (2007), 1079-1099, 6.8, Elsevier.
Lee, F. Y. F., et al. "Clinical Pharmacokinetics of Oral CCNU (Lomustine)." Cancer Chemotherapy and Pharmacology, (1985), 125-131, 14.2, Springer Nature.
Funaro, J. et al. "A costly rebranding of an old drug comes with a 700% price increase." The Cancer Letter, (2017).
Webb, D. et al. "Continuous Flow Multi-Step Organic Synthesis." Chemical Science, (2010), 675-680, 1.6, The Royal Society of Chemistry.
Wegner, J. et al. "Ten Key Issues in Modern Flow Chemistry." Chemical Communications, (2011), 4583-4592, 47.16, The Royal Society of Chemistry.
Yoshida, J. et al. "Green and Sustainable Chemical Synthesis Using Flow Microreactors." ChemSusChem, (2011), 331-340, 4.3, John Wiley & Sons, Ltd.
Yoshida, J. et al. "Flash Chemistry: Flow Chemistry That Cannot Be Done in Batch." Chemical Communications, (2013), 9896-9904, 49.85, The Royal Society of Chemistry.
Hessel, V., et al. "Novel Process Windows for Enabling, Accelerating, and Uplifting Flow Chemistry." ChemSusChem (2013), 746-789, 6.5, John Wiley & Sons, Ltd.
Jensen, K. F. et al. "Tools for Chemical Synthesis in Microsystems." Lab on a Chip, (2014), 3206-3212, 14.17, The Royal Society of Chemistry.
Gutmann, B. et al. "Continuous-Flow Technology—A Tool for the Safe Manufacturing of Active Pharmaceutical Ingredients." Angewandte Chemie International Edition, (2015), 6688-6728, 54.23, John Wiley & Sons, Ltd.
Cambie, D., et al. "Applications of Continuous-Flow Photochemistry in Organic Synthesis, Material Science, and Water Treatment." Chemical Reviews, (2016), 10276-10341, 116.17, American Chemical Society.
Poh, J.S., et al. "Rapid Asymmetric Synthesis of Disubstituted Allenes by Coupling of Flow-Generated Diazo Compounds and Propargylated Amines." Angewandte Chemie International Edition, (2017),1864-1868, 56.7, John Wiley & Sons, Ltd.
Yu, Z., et al. "A Fully Continuous-Flow Process for the Synthesis of p-Cresol: Impurity Analysis and Process Optimization." Organic Process Research & Development, (2017),1644-1652, 21.10, American Chemical Society.
Britton, J. et al. "Multi-Step Continuous-Flow Synthesis." Chemical Society Reviews, (2017),1250-1271, 46.5, The Royal Society of Chemistry.
Berton, M. et al. "On-Demand Synthesis of Organozinc Halides under Continuous Flow Conditions." Nature Protocols, (2018), 324-334, 13.2. Springer Nature.
Hessel, V. "Novel Process Windows—Gate to Maximizing Process Intensification via Flow Chemistry." Chemical Engineering & Technology, (2009), 1655-1681, 32.11, John Wiley & Sons, Ltd.
Zaborenko, N., et al. "Kinetic and Scale-Up Investigations of Epoxide Aminolysis in Microreactors at High Temperatures and Pressures." Organic Process Research & Development, (2011), 131-139, 15.1, American Chemical Society.
Wiles, C. et al. "Recent Advances in Micro Reaction Technology." Chemical Communications, (2011), 6512-6535, 47.23, The Royal Society of Chemistry.
Wegner, J. et al. "Flow Chemistry—A Key Enabling Technology for (Multistep) Organic Synthesis." Advanced Synthesis & Catalysis, (2012), 17-57, 354.1, John Wiley & Sons, Ltd.

Snead, D. R. et al. "End-to-End Continuous Flow Synthesis and Purification of Diphenhydramine Hydrochloride Featuring Atom Economy, in-Line Separation, and Flow of Molten Ammonium Salts." Chemical Science, (2013), 2822-2827, 4.7, The Royal Society of Chemistry.
Len, C. et al. "Palladium-Catalyzed Suzuki-Miyaura Cross-Coupling in Continuous Flow." Catalysts, (2017), 146, 7.5.
Lummiss, J. A. M., et al. "Towards More Efficient, Greener Syntheses through Flow Chemistry." The Chemical Record, (2017), 667-680, 17.7, John Wiley & Sons, Ltd.
Morse, P. D. et al. "Synthesis and Utilization of Nitroalkyne Equivalents in Batch and Continuous Flow." Angewandte Chemie International Edition, (2017), 13999-14002, 56.45, John Wiley & Sons, Ltd.
Gustafsson, T. et al. "Trimethylaluminium Mediated Amide Bond Formation in a Continuous Flow Microreactor as Key to the Synthesis of Rimonabant and Efaproxiral." Chemical Communications, (2008), 1100-1102, 9, The Royal Society of Chemistry.
Hopkin, M. D. et al. "An Expeditious Synthesis of Imatinib and Analogues Utilising Flow Chemistry Methods." Organic & Biomolecular Chemistry, (2013), 1822-1839, 11.11, The Royal Society of Chemistry.
Deadman, B. J., et al. "The Synthesis of Bcr-Abl Inhibiting Anti-cancer Pharmaceutical Agents Imatinib, Nilotinib and Dasatinib." Organic & Biomolecular Chemistry, (2013), 1766-1800, 11.11, The Royal Society of Chemistry.
Murray, P. R. D., et al. "Continuous Flow-Processing of Organometallic Reagents Using an Advanced Peristaltic Pumping System and the Telescoped Flow Synthesis of (E/Z)-Tamoxifen." Organic Process Research & Development, (2013), 1192-1208, 17.9, American Chemical Society.
Zhang, P. et al. "Continuous Flow Total Synthesis of Rufinamide." Organic Process Research & Development, (2014), 1567-1570, 18.11, American Chemical Society.
Snead, D. R. et al. "A Three-Minute Synthesis and Purification of Ibuprofen: Pushing the Limits of Continuous-Flow Processing." Angewandte Chemie International Edition, (2015), 983-987, 54.3, John Wiley & Sons, Ltd.
Adamo, A., et al. "On-Demand Continuous-Flow Production of Pharmaceuticals in a Compact, Reconfigurable System." Science, (2016), 61-67, 352.6281, The American Association for the Advancement of Science.
Lin, H., et al. "A Rapid Total Synthesis of Ciprofloxacin Hydrochloride in Continuous Flow." Angewandte Chemie International Edition, (2017), 8870-8873, 56.30, John Wiley & Sons, Ltd.
Zhang, P., et al. "Advanced Continuous Flow Platform for On-Demand Pharmaceutical Manufacturing." Chemistry—A European Journal, (2018), 2776-2784, 24.11, John Wiley & Sons, Ltd.
Falcone, C. E., et al. "Reaction Screening and Optimization of Continuous-Flow Atropine Synthesis by Preparative Electrospray Mass Spectrometry." Analyst, (2017), 2836-2845, 142.15, The Royal Society of Chemistry.
Loren, B. P., et al. "Mass Spectrometric Directed System for the Continuous-Flow Synthesis and Purification of Diphenhydramine." Chemical Science, (2017), 4363-4370, 8.6, The Royal Society of Chemistry.
Wleklinski, M., et al. "Can Accelerated Reactions in Droplets Guide Chemistry at Scale?" European Journal of Organic Chemistry, (2016), 5480-5484, 2016.33, John Wiley & Sons, Ltd.
Ewan, H. S., et al. "Multistep Flow Synthesis of Diazepam Guided by Droplet-Accelerated Reaction Screening with Mechanistic Insights from Rapid Mass Spectrometry Analysis." Organic Process Research & Development, (2017), 1566-1570, 21.10, American Chemical Society.
Riva, E., et al. "Synthesis of (+)-Dumetorine and Congeners by Using Flow Chemistry Technologies." Chemistry—A European Journal, (2011), 6221-6226, 17.22, John Wiley & Sons, Ltd.
Ahmed-Omer, B. et al. "Preparation of Fluoxetine by Multiple Flow Processing Steps." Organic & Biomolecular Chemistry, (2011), 3854-3862, 9.10, The Royal Society of Chemistry.
Newton, S., et al. "Accelerating Spirocyclic Polyketide Synthesis Using Flow Chemistry." Angewandte Chemie International Edition, (2014), 4915-4920, 53.19, John Wiley & Sons, Ltd.

(56) References Cited

OTHER PUBLICATIONS

Peeva, L., et al. "Continuous Consecutive Reactions with Inter-Reaction Solvent Exchange by Membrane Separation." Angewandte Chemie International Edition, (2016), 13576-13579, 55.43, John Wiley & Sons, Ltd.

Brasholz, M., et al. "A Gram-Scale Batch and Flow Total Synthesis of Perhydrohistrionicotoxin." Chemistry—A European Journal, (2010), 11471-11480, 16.37, John Wiley & Sons, Ltd.

Jensen, K. F. "Silicon-Based Microchemical Systems: Characteristics and Applications." MRS Bulletin, (2006), 101-107, 31.2, Cambridge University Press.

Geyer, K. et al. "Developing Continuous-Flow Microreactors as Tools for Synthetic Chemists." Synlett, (2009), 2382-2391, 15, Georg Thieme Verlag KG.

Kim, H., et al. "Submillisecond Organic Synthesis: Outpacing Fries Rearrangement through Microfluidic Rapid Mixing." Science, (2016), 691-694, 352.6286, The American Association for the Advancement of Science.

Troshin, K. et al. "Snap Deconvolution: An Informatics Approach to High-Throughput Discovery of Catalytic Reactions." Science, (2017), 175-181, 357.6347, The American Association for the Advancement of Science.

Wleklinski, M., et al. "High Throughput Reaction Screening Using Desorption Electrospray Ionization Mass Spectrometry." Chemical Science, (2018), 1647-1653, 9.6, The Royal Society of Chemistry.

Jaman, Z., et al. "High Throughput Experimentation and Continuous Flow Validation of Suzuki-Miyaura Cross-Coupling Reactions." Chemistry—A European Journal, (2018), 9546-9554, 24.38, John Wiley & Sons, Ltd.

Yan, X. et al. "Organic Reactions in Microdroplets: Reaction Acceleration Revealed by Mass Spectrometry." Angewandte Chemie International Edition, (2016), 12960-12972, 55.42, John Wiley & Sons, Ltd.

Ifa, D. R., et al. "Latent Fingerprint Chemical Imaging by Mass Spectrometry." Science, (2008), 805, 321.5890, The American Association for the Advancement of Science.

Freeman, E. S. "The Kinetics of the Thermal Decomposition of Sodium Nitrate and of the Reaction between Sodium Nitrite and Oxygen." Journal of Physical Chemistry, (1956), 1487-1493, 60.11, American Chemical Society.

Fox, J. B. et al. "The Determination of Nitrite: A Critical Review." CRC Critical Reviews in Analytical Chemistry, (1985), 283-313, 15.3, Taylor & Francis.

Johnston, T. P. et al. "Synthesis of Chlorozotocin, the 2-Chloroethyl Analog of the Anticancer Antibiotic Streptozotocin." Journal of Medicinal Chemistry, (1975), 104-106, 18.1, American Chemical Society.

Baracu, I. et al. "Potential Anticancer Agents. XXVIII. Synthesis of Some Cyclohexanone Derived N-Nitrosoureas." Journal für Praktische Chemie, (1985), 675-681, 327.4, John Wiley & Sons, Ltd.

\* cited by examiner

ON-DEMAND RAPID SYNTHESIS OF LOMUSTINE UNDER CONTINUOUS FLOW CONDITIONS

GOVERNMENT SUPPORT

This invention was made with government support under CA023168 awarded by National Institutes of Health, and W911NF-16-2-0020 awarded by Army Research Laboratory. The government has certain right in the invention.

FIELD OF INVENTION

This disclosure provides a novel method of synthesizing lomustine drug in scalable size under continuous flow conditions. Particularly, lomustine is prepared via a linear sequence of two chemical reactions performed separately in two telescoped flow reactors. The process omits isolation and purification of a labile intermediate, providing tremendous advantages of producing active pharmaceutical ingredient at low cost.

BACKGROUND

Lomustine, a widely used anticancer agent, is a highly lipophilic alkylating agent that produces chloroethyl carbonium ions and carbamylating intermediates in vivo.[1] These electrophilic compounds attack the nucleophilic sites on DNA to form alkylated products.[1a] Other anticancer agents such as mitomycin C, streptonigrin, bleomycin, and the anthracyclines require bioactivation to react with their cellular targets, whereas lomustine does not require pre-activation.[2] Unlike alkylating agents that form adducts at the most reactive $N^7$ position of guanine, chloroethylating compounds like lomustine form adducts at $O^6$, leading to interstrand DNA cross-linking. If DNA repair does not occur, this crosslinking can cause double strand breaks during DNA replication, eventually leading to cell death via apoptosis.[3]

Lomustine, 1-(2-chloroethyl)-3-cyclohexyl-1-nitrosourea (commercial names: CCNU, CeeNU, Gleostine) is used as an oral antineoplastic agent that is administered every 6 weeks. It was first evaluated in clinical trials in the late 1960s[4] and approved by the US FDA in 1976[5] for primary and metastatic brain tumors as well as Hodgkin's lymphoma.[3] Bristol-Myers Squibb originally held the patent for the agent under the brand name CeeNu. In 2014, Next Source Biotechnology LLC (NSB) was approved by the FDA for the rebranding of lomustine under the trade name Gleostine.[5] The average wholesale price for one dose of rebranded Gleostine is $1,645.68, while the generic formulation costs $203.38.[5] The huge price discrepancy (700%) between Gleostine and the generic formulation has created patient access problems, thus motivating our effort to develop a rapid and low cost lomustine synthesis method by continuous flow.

Continuous flow synthesis has been reported as an efficient methodology and has been explored in both industry and academic labs for the last few decades:[6] Compared to traditional batch synthesis processes, flow reactors provide better control over reaction conditions and selectivity owing to rapid mixing and precise control of reaction parameters such as temperature, stoichiometry, pressure, and residence time. The enhanced heat and mass transfer capabilities also provide safer and greener operational conditions:[6b, 7] Generally, these aspects of continuous flow synthesis contribute to improved chemical reaction efficiency[7g, 8] and shorter reaction times, enabling process intensification[7a], and more facile scale-up, with improved quality and consistency in production. Motivated by these factors, continuous flow synthesis of active pharmaceutical ingredient has recently become more attractive,[7g, 9] however efficient execution of multistep reactions in a telescoped manner still remains a challenge due to challenges arising from workup conditions[9f, 10], solvent switches,[11] and flow rate differences.[11a, 12] Moreover, optimization of continuous flow conditions and analysis require significant investments in time and material.[9f, 13]

SUMMARY OF THE INVENTION

This disclosure provides a method of producing Lomustine with continuous flow condition, the method comprises the steps illustrated in FIG. 6, or steps illustrated in FIG. 20.

This disclosure further provides a method of identifying optimum reaction condition of producing Lomustine. The method comprises screening the reaction condition according to scheme 1 in a continuous flow as a function of temperature, solvent and stoichiometry, wherein the reaction is monitored by TLC and MS using a triple quadrupole mass spectrometer operating in positive ion mode to afford rapid investigation of full mass spectra and product ion distribution for each reaction condition.

This disclosure further provides a system for telescoped Lomustine synthesis. The system comprises sequentially:
- a first telescoping chamber mixing cyclohexylamine (1) and 1-chloro-2-isocyanatoethane (2) with triethyalamine (TEA) at 50 C for about 1 minute;
- a Zaiput liquid-liquid extractor to couple with the first telescoping chamber to remove the base TEA from the first reaction chamber; and
- a second telescoping chamber for nitrosation of the intermediate product 1-(2-chloroethyl) -3-cyclohexylurea (3) at 25 C for about 8 minutes using tBuONO (5) as the nitrosation agent.

These and other features, aspects and advantages of the present invention will become better understood with reference to the following figures, associated descriptions and claims.

DETAILED DESCRIPTION

Figure 1:
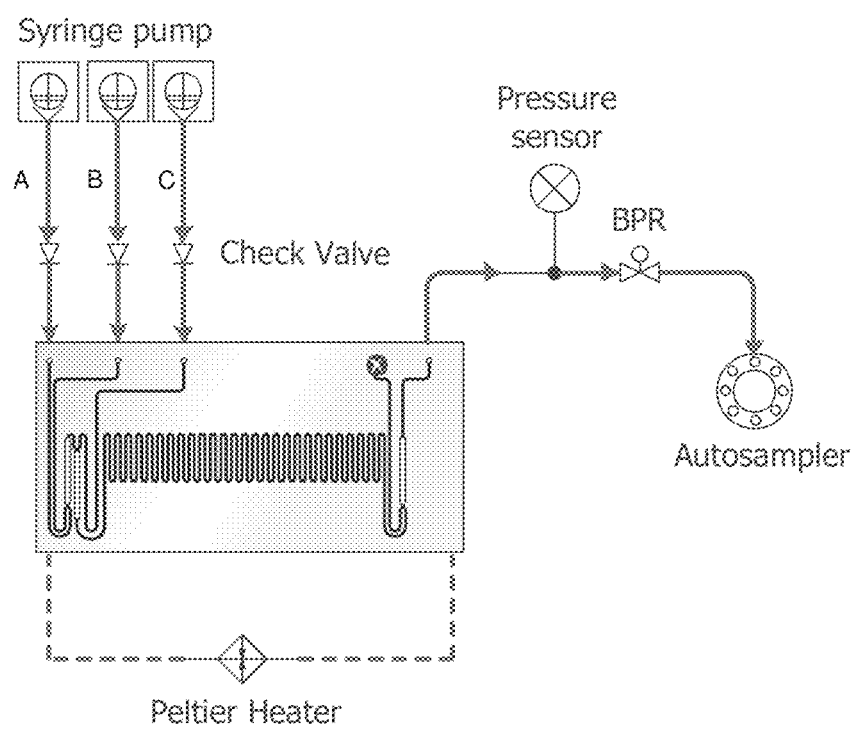
FIG. 1: Microfluidic synthesis of intermediate 3 in a glass reactor chip (SOR 3225). A=1 in THF; B=2 in THF, C=TEA in THF.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Lomustine, an important agent for treatment of brain tumors and Hodgkin's lymphoma, has been synthesized using continuous flow methodology. Desorption electrospray ionization mass spectrometry (DESI-MS) was used to quickly explore a large number of reaction conditions and guide the efficient translation of optimized conditions to continuous lomustine production at a rate of approximately one dose/h. Using only four inexpensive commercially available starting materials and a total residence time of 9 min, lomustine was prepared via a linear sequence of two chemical reactions performed separately in two telescoped flow reactors. Sequential offline extraction and filtration resulted in 63% overall yield of pure lomustine at a production rate of 110 mg/h. The primary advantage of this approach lies in the rapid manufacture of lomustine with two telescoped steps to avoid isolation and purification of a labile intermediate, thereby decreasing the production cost of this active pharmaceutical ingredient to approximately $5/gram in total material cost.

Briefly, herein we disclose robust high throughput reaction screening method using desorption electrospray ionization mass spectrometry (DESI-MS) to guide scalable synthesis in continuous flow reactors at scale.[13e] Herein, we report the continuous flow synthesis of lomustine using an optimization protocol that was guided by DESI-MS. The final method consists of two reactions telescoped without isolation or purification of intermediates. This approach can reduce production costs radically by using a simple reactor set up and inexpensive starting materials (Scheme 1). To the best of our knowledge, this is the first synthesis of lomustine telescoped in continuous flow using an approach that does not interrupt the flow sequence due to intermediate workup requirements.

Scheme 1: Synthesis plan for lomustine in continuous flow, where 4 = NaNO₂/HCO₂H and 5 = tBuONO Continuous Synthesis of 1-(2-Chloroethyl)-3-cyclohexylurea, 3.

The first step in the synthesis of lomustine (Scheme 1) is a fast reaction at room temperature. This transformation was optimized in continuous flow as a function of temperature, solvent, and stoichiometry to discover the conditions for maximum product yield. The reactions were monitored by TLC and MS using a triple quadrupole mass spectrometer operating in positive ion mode to afford rapid investigation of full mass spectra and product ion distribution for each reaction condition.

TABLE 1

Reaction conditions evaluated for the synthesis of 3 in flow using a Chemtrix S1 glass system fitted with a 3225 SOR reactor chip.

| Entry | Solvent | 2 equivalent | Temperature, ° C. | Residence time, sec | Isolated Yield % |
|---|---|---|---|---|---|
| 1 | EtOH | 1 | 50 | 10 | 42.8 |
| 2 | EtOH | 1 | 50 | 30 | 0.00 |
| 3 | EtOH | 1 | 50 | 60 | 0.00 |
| 4 | ACN | 1 | 50 | 10 | 56.2 |
| 5 | ACN | 1 | 50 | 30 | clogged |
| 6 | ACN | 1 | 25 | 30 | clogged |
| 7 | Toluene | 1 | 50 | 10 | clogged |
| 8 | Ether | 1 | 50 | 10 | clogged |
| 9 | THF | 1 | 25 | 10 | 50.0 |
| 10 | THF | 1 | 25 | 30 | 56.4 |
| 11 | THF | 1 | 50 | 10 | 59.5 |
| 12 | THF | 1 | 50 | 30 | 62.1 |
| 13 | THF | 1 | 65 | 10 | 47.5 |
| 14 | THF | 1 | 65 | 30 | 29.1 |
| 15 | THF | 1.2 | 50 | 10 | 61.2 |
| 16 | THF | 1.2 | 50 | 30 | 64.8 |
| 17 | THF | 1.2 | 50 | 60 | 71.3 |
| 18 | THF | 1.4 | 50 | 10 | 67.1 |
| 19 | THF | 1.4 | 50 | 30 | 82.0 |
| 20 | THF | 1.4 | 50 | 60 | 91.7 |
| 21 | THF | 1.4 | 50 | 180 | 82.8 |

A cascade method was designed to reveal the best conditions for the first step. Cyclohexylamine, 1, 1-chloro-2-isocyanatoethane, 2, and triethylamine (TEA) solutions were pumped through a Chemtrix 3225 SOR chip with automatic collection of the products in vials via an autosampler (FIG. 1). The individual reaction mixtures were evaporated and the white solid washed with cold $Et_2O$ before drying under vacuum for overnight prior to analysis by TLC, MS, MS/MS, and NMR ($^1H$ and $^{13}C$).

Parameters such as residence time (t), reaction temperature (T), 1-chloro-2-isocyanatoethane:cyclohexylamine ratio were investigated systematically under continuous flow conditions. As shown in Table 1, product yield dropped sharply in EtOH at longer residence times (entries 1-3) due to ethanolysis of the 1-chloro-2-isocyanato-ethane starting material. Though the yield of 3 in ACN was significant, its low solubility in this solvent led to significant chip clogging (entries 4-6). Similar clogging problems were found for toluene and $Et_2O$, even at low concentrations (entries 7-8). The yield increased to 50-62% with longer residence times (entries 9-14) in THF, reaching a maximum when τ=30 s at 50° C. and decayed rapidly with increased temperature (entries 13, 14) due to increased product decomposition at elevated temperature. The yield of 3 was also found to increase with proportions of 2 ratio (entries 15-21), whereas longer residence times promoted product decomposition (entry 21). Consequently, a maximum yield of intermediate 3 (92%) was achieved under conditions of τ=60 s, T=50° C., and 1.4 equivalents of 1-chloro-2-isocyanatoethane (entry 20).

Synthesis of Lomustine, Guided by DESI-MS High Throughput Experimentation.

We employed DESI-MS to evaluate the impact of solvent, concentration and nitrosation reagent type on the efficiency of lomustine production. DESI-MS was originally applied to the surface analysis of intact samples such as biological tissues for cancer diagnosis or human fingerprints for drug detection,[14] although more recently, the DESI-MS approach has been used for reaction analysis.[13e] This approach is based on the phenomena of reaction acceleration that occurs within confined volumes such as microdroplets that originate from spray-based MS ionization processes.[14a] MS analysis speeds approaching 10,000 reaction spots/hour can be achieved by this technique.[13e]

As shown in Scheme 1 ($2^{nd}$ step), two nitrosation methods were investigated. First, the efficiency of sodium nitrite, 4, in formic acid as the nitrosation reagent toward the conversion of 3 to lomustine was evaluated. This conversion was then compared with tert-butyl nitrite (TBN, 5) as the nitrosation reagent.

Figure 2:
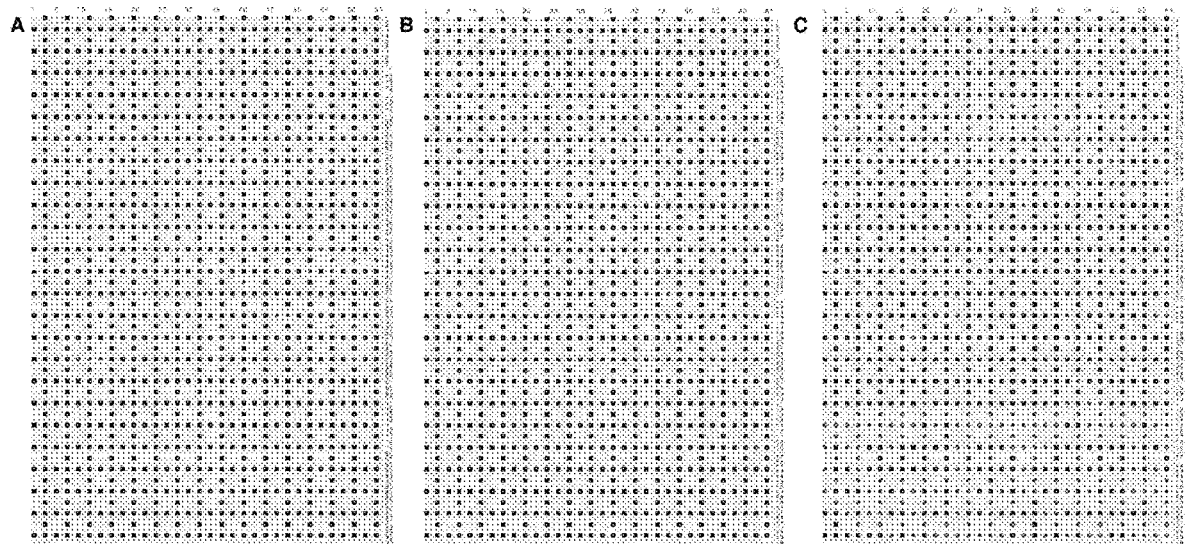
FIG. 2: DESI-MS plate maps showing the presence or absence of expected ions at each spot where the nitrosation reaction conditions were tested using different stoichiometries and with commercially available standards. Blue dots indicate the presence of the m/z 169 expected stable fragment for the reaction product (successful reaction), Red dots indicate that the expected m/z for the reaction product was not present at the reaction spot (unsuccessful reaction condition). A: Concentration screening using the lomustine ion (m/z 169) intensity and $NaNO_2$ as nitrosation reagent; B: Solvent screening using the lomustine ion (m/z 169) intensity and $NaNO_2$ as nitrosation reagent; C: Solvent screening using the lomustine ion (m/z 169) intensity and tBuONO as nitrosation reagent.

DESI-MS was used to evaluate the $NaNO_2/HCO_2H$ transformation under different reactant concentrations and solvents. The expected m/z 234 value for lomustine were not observed. Analysis of a commercial lomustine sample yielded a very similar MS, suggesting that loss of NO occurs readily during the ionization process. Triple quadrupole MS with electrospray ionization, as well as ion trap mass spectrometry coupled with DESI, revealed the presence of a stable lomustine ion at m/z 169. This was further confirmed by the fact that the losmustine fragments from this reaction matched with commercially available lomustine. Reactions for all $NaNO_2$ concentrations in $THF:H_2O$ worked better than for $ACN:H_2O$ (FIG. 2, A). Also, the fragments from 3 were most abundant in the $ACN:H_2O$ reactions compared to reactions in $THF:H_2O$, suggesting that the conversion of starting material was comparatively sluggish in $ACN:H_2O$. Next, eight different solvents (EtOH, MeOH, DCM, ACN, toluene, DMSO, THF and EtOAc) were compared for guiding the continuous flow synthesis. All eight solvents produced similar outcomes using 4 as the nitrosation reagent (FIG. 2, B). When 5 was used, lomustine was detected in all solvents except THF and EtOAc (FIG. 2, C).

Nitrosation Reaction Optimization in Continuous Flow.

We utilized the reaction conditions emerging from the DESI-MS high throughput experiments to optimize the flow synthesis and also check whether unsuccessful reactions identified by DESI-MS would also negatively translate under flow conditions. From the DESI-MS experiments, THF was identified as the best solvent for nitrosation using 4. Excess 4 was also used to maximize conversion of 3 to lomustine since the nitrosation reagents are hygroscopic and readily oxidize to nitrate.[15] Overall, the DESI-MS experiments were in excellent agreement with the outcomes of flow reaction conditions in terms of stoichiometry, reagents and solvents.

Figure 3:
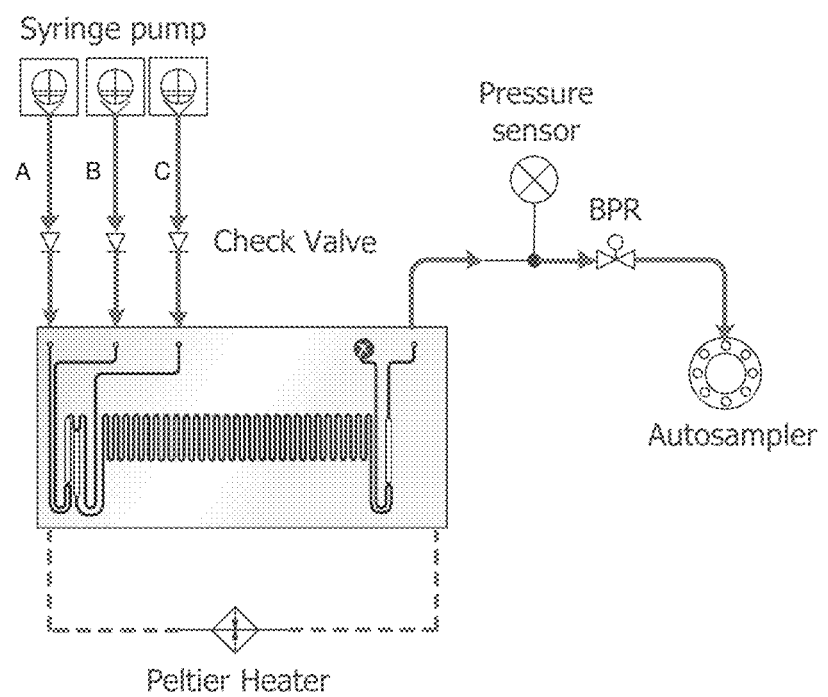
FIG. 3: Microfluidic synthesis of lomustine using $NaNO_2$/ $HCO_2H$ as nitrosation reagent in a Chemtrix 3225 SOR glass reactor chip. A=3 in THF; B=$HCO_2H$ (neat), C=$NaNO_2$ in $MeOH:H_2O$ (4:1).

A series of reactions (Table 2) were performed to maximize the conversion of 3 to lomustine under continuous synthesis conditions (FIG. 3). Initially, we examined the reaction at 0° C. with a residence time of 30 sec using TLC and MS to monitor the reaction progress. Gratifyingly, lomustine was obtained through this very short reaction time, albeit in low conversion (Table 2, entry 1). A systematic evaluation of residence times led to good lomustine yields and starting material conversions, however, longer residence times appeared enhance the decomposition of lomustine (Table 2, entries 2-6). Consequently, we kept the temperature constant at 0° C. to avoid NaNO₂ decomposition of sodium nitrite to the diazonium salt that occurs at higher temperatures.[15b]

Different purification methods were evaluated to isolate pure lomustine. At first, the product was extracted with Et₂O (3 times) to exploit the low solubility of 3 in this solvent (Method 1). Unfortunately, the TLC analysis revealed the presence of 3 in the organic layer as well as in the aqueous layer. Therefore, the combined organic extracts were dried over anhydrous Na₂SO₄ and concentrated in vacuo to produce a yellowish oil that re-dissolved in Et₂O, heated and cooled in an ice bath to precipitate 3 from the mixture. NMR analysis of the filtrate revealed that 22% of 3 remained in the isolated lomustine product. Next, we purified the product by recrystallization from ACN (Method 2). Although we obtained very pure lomustine as identified by NMR analysis, recovery using this approach was low. Finally, we found that hot filtration from petroleum ether removed the insoluble 3 impurity (Method 3). Concentration of the filtrate after drying gave pure lomustine without detectable amount of 3 by NMR. Using this method, we obtained 74% isolated yield of pure lomustine under the conditions of 0° C. reaction and a residence time of 5 min using 3 equivalents of 4.

TABLE 2

Isolated yields of lomustine under different reaction conditions using 4 as the nitrosation reagent. Temperture = 0° C., solvent = MeOH:H₂O (4:1)

| Entry | Residence time, min | Isolated Yield (Method 1) % | Isolated Yield (Method 2) % | Isolated Yield (Method 3) % |
|---|---|---|---|---|
| 1 | 0.5 | 26.8 | — | 43.7 |
| 2 | 1 | 48.8 | — | 50.6 |
| 3 | 3 | 51.6 | 41.2 | 63.1 |
| 4 | 5 | 79.0 | 54.4 | 74.5 |
| 5 | 8 | 59.0 | — | 68.7 |
| 6 | 10 | 50.2 | — | 65.3 |

Figure 4:
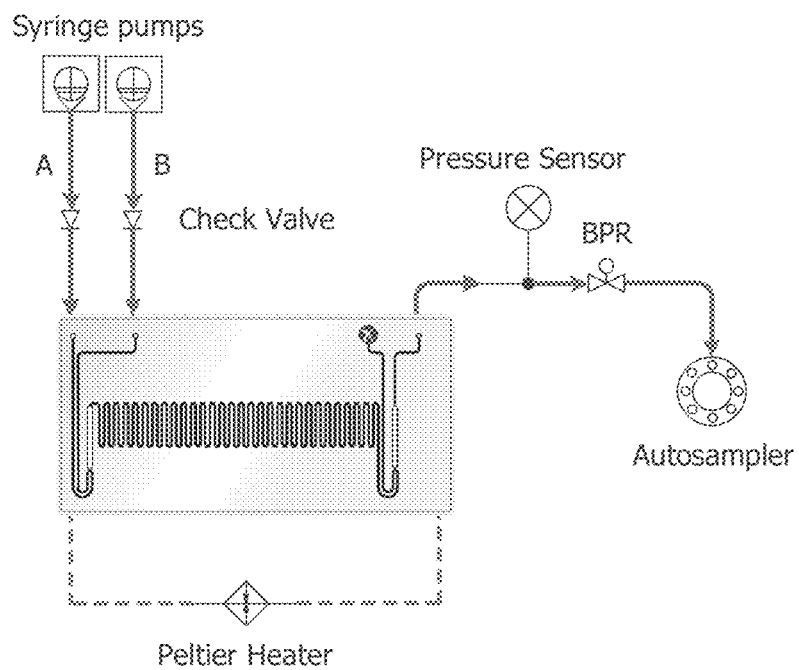
FIG. 4: Microfluidic synthesis of lomustine using 5 as nitrosation reagent in a Chemtrix 3223 SOR glass reactor chip. A=3 in ACN:EtOH (3.7:1) ; B=5 in ACN.

The reaction was also optimized with respect to residence time, temperature, and solvent using 5 as nitrosation agent (FIG. 4 and Table 3). This optimization process led to the finding that an elevated residence time (8 min), lower temperature (25° C.) and increased 5 ratio (3 equiv) resulted in the most efficient conversion to lomustine (91% isolated yield) after Method 3 purification (Table 3, entry 11).

TABLE 3

Synthesis of lomustine under at different reaction conditions using 5 as the nitrosation reagent.

| Entry | Solvent (3.7:1) | Temperature, (° C.) | Residence time, (min) | Isolated Lomustine Yield (%) |
|---|---|---|---|---|
| 1 | ACN:EtOH | 50 | 0.5 | 68.3 |
| 2 | ACN:EtOH | 50 | 1 | 69.8 |
| 3 | ACN:EtOH | 50 | 3 | 60.0 |
| 4 | ACN:EtOH | 50 | 5 | 58.8 |
| 5 | ACN:EtOH | 50 | 8 | 51.9 |
| 6 | ACN:EtOH | 50 | 10 | 49.4 |
| 7 | ACN:EtOH | 25 | 0.5 | 48.8 |
| 8 | ACN:EtOH | 25 | 1 | 54.1 |
| 9 | ACN:EtOH | 25 | 3 | 66.5 |
| 10 | ACN:EtOH | 25 | 5 | 79.3 |
| 11 | ACN:EtOH | 25 | 8 | 91.2 |
| 12 | ACN:EtOH | 25 | 10 | 89.8 |
| 13 | THF(100%) | 25 | 3 | 36.5 |

Telescoped Synthesis of Lomustine

Figure 5:
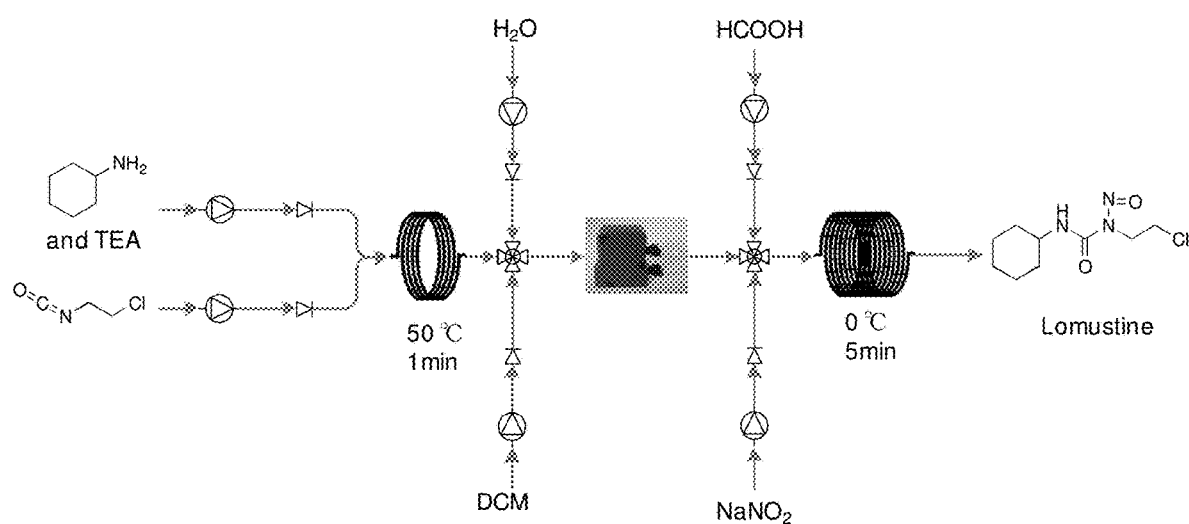
FIG. 5: Schematic for the telescoped synthesis of lomustine using NaNO₂/HCO₂H (4) as nitrosation reagent.

The next step was to adapt the whole two step sequence to a continuous flow setup. We sought to telescope the carbamylation and nitrosation reactions using the Chemtrix reactor chips, however, an extraction needed to be incorporated between the steps to remove the TEA present in the first reaction to avoid competitive consumption of the nitrosation reagent in the second step. We achieved this objective by incorporating a commercially available Zaiput liquid-liquid extractor to remove the base before the nitrosation step and by re-optimizing the synthesis using FEP tubing reactors (FIG. 5). In the beginning, the best reaction conditions were a 1 min residence time at 50° C. for the first step and a 5 min residence time at 0° C. for the second step, yielding 43 mg (51.8% overall yield) of pure lomustine (Table 4, entry 1). Efforts to improve the lomustine yield by changing the residence times of either the first or second steps were unsuccessful in the FEP tubing reactor using 4 as nitrosation reagent (Table 4, entry 1-4).

TABLE 4

Lomustine synthesis yields for telescoped reactions under different eagents, residence time, stoichiometry, and temperature conditions.

| Entry | Nitrosation reagent | Step 1 | Step 2 | TEA Stoichiometry | Isolated Lomustine Yield % |
|---|---|---|---|---|---|
| 1 | 4 | 1 min, 50° C. | 5 min, 0° C. | 1 | 51.8 |
| 2 | 4 | 2 min, 50° C. | 5 min, 0° C. | 1 | 44.2 |
| 3 | 4 | 10 min, 50° C. | 5 min, 0° C. | 1 | 38.6 |
| 4 | 4 | 10 min, 50° C. | 3 min, 0° C. | 1 | 24.0 |
| 5 | 5 | 1 min, 50° C. | 5 min, 50° C. | 1 | 41.5 |
| 6 | 5 | 1 min, 50° C. | 5 min, 25° C. | 1 | 21.8 |
| 7 | 5 | 1 min, 50° C. | 8 min, 25° C. | 1 | 24.6 |
| 8 | 5 | 1 min, 50° C. | 8 min, 25° C. | 0.1 | 55.5 |
| 9 | 5 | 1 min, 50° C. | 8 min, 25° C. | 0.01 | 63.7 |

Figure 6:
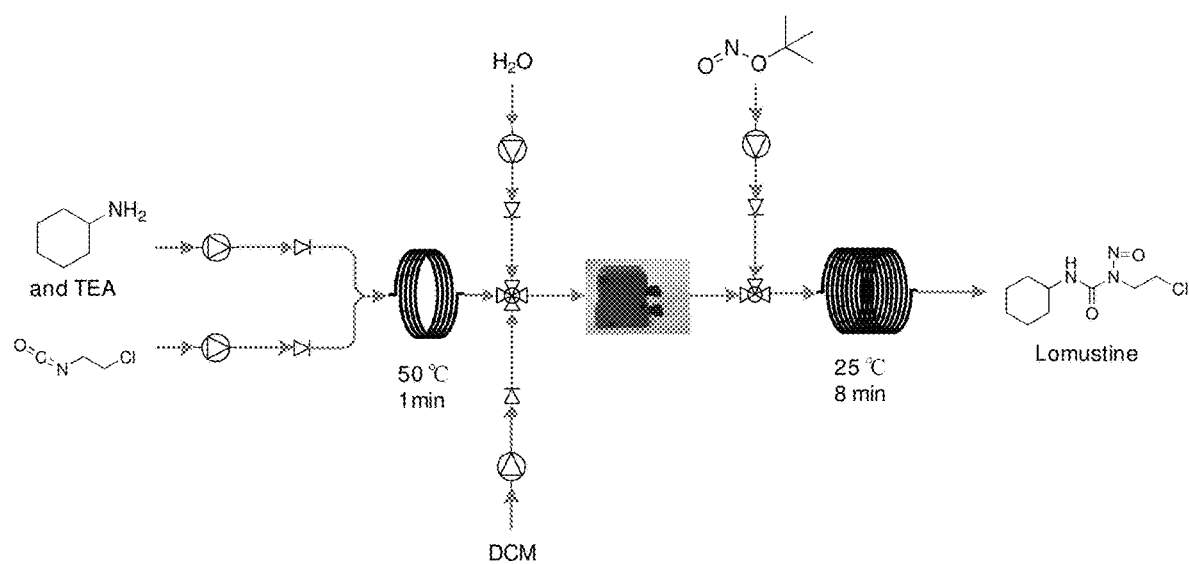
FIG. 6: Schematic for the final telescoped synthesis of lomustine using 5 as a nitrosation reagent.

Subsequent telescoping experiments indicated that 5 was a better nitrosation reagent than 4 for the efficient synthesis of lomustine in flow. This is also true when the synthesis of lomustine were performed separately in glass reactor chips (Table 2 and 3). The final optimized conditions were 1 min reaction time at 50° C. for the first step and 8 min reaction time at 25° C. for the second step (FIG. 6). As the small amount of extracted TEA from the first step minimized the TBN activity, lowering the amount of TEA used led to an increased production of lomustine (Table 4, entries 7-9) such that 1% TEA produced 110 mg (63%) of pure isolate lomustine via this reaction setup (Table 4, entry 9). TLC, NMR ($^1$H and $^{13}$C), MS and MS/MS data of lomustine obtained by this telescoped continuous route were a direct match with values measured for commercially available lomustine.

Figure 7:
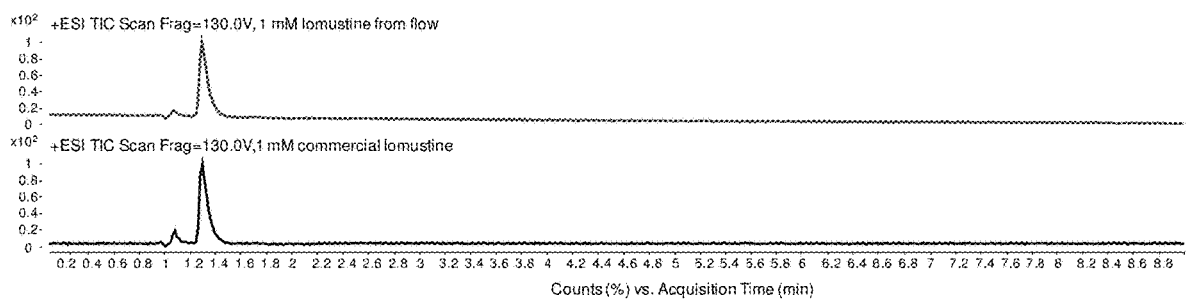
FIG. 7: Total ion chromatogram (TIC) from HPLC-MS/MS and comparison between synthesized lomustine (top, red) and commercially available lomustine (bottom, black).

HPLC-MS was used to certify the purity of the synthesized lomustine and compare the total ion chromatogram (TIC) values of this material with a commercial lomustine standard. The TIC profile fully overlapped with the commercial standard without the appearance of any new byproducts (FIG. 7).

We have developed a rapid continuous synthesis of lomustine using DESI-MS to guide the selection of reaction conditions in the second step of the two step overall transformation. The total residence time is 9 minutes to produce pure lomustine in 63% overall isolated yield compared to over 2 hours to generate a lower product yield using batch conditions.[1b, 2, 16] The two synthetic steps were optimized separately in glass chips and then translated to FEP tubing for telescoped scaling of the whole process. Only one in-line workup step was required for the two-step reaction sequence. Mixed solvents were used in the telescoped reaction to avoid clogging due to the low solubility of 3. tButyl nitrite, 5, was found to be a milder and more efficient nitrosation reagent in this process to enable the isolation of pure lomustine via simple extraction, filtration and washing. This synthesis is a faster and greener process that affords a significant reduction in reaction time, lower waste production, and avoidance of any chromatographic steps. Using this method, 110 mg/hour of lomustine can be produced, equivalent to one dose/h for an agent that is administered orally every 6 weeks. Scale up and in-line recrystallization of lomustine are in progress.

Supporting Information

Materials

All chemicals and reagents were purchased from Sigma-Aldrich (St Louis, Mo.) and used without any purification. Intermediate 3 standard was purchased from 1Click Chemistry, Inc. (Kendall Park, N.J.). Lomustine was purchased from ApexBio (Houston, Tex.).

Liquid Handling Robot

Assay plate set up and sample preparation steps for DESI-MS were done using a Biomek i7 (Beckman Coulter, Inc., Indianapolis, Ind.) dual-bridge liquid handling robot. A 384-tip head was employed to enable simultaneous transfer of 384 samples under the same conditions (speed of aspiration and dispensing, height of pipetting at source and destination positions, pattern of pipetting, etc.). An 8-channel head was used to provide more flexibility in terms of volumes transferred, layout of source and destination places, pipetting height, speed, and reaction stoichiometry. The high capacity deck accommodated all labware (robotic tips, plates, reservoirs) needed for assembling one reaction step. All robotic tips were made of chemically resistant polypropylene and disposable. Polypropylene multi-well plates and reservoirs, as well as custom made Teflon reservoirs were used during the experiments for reagent solutions. Methods were developed and validated using the Biomek point-and-click programming tool. Standard pipetting techniques used in this software were modified to optimize accurate transfer of highly volatile liquids.

Mass Spectrometry

Samples were analyzed using a Thermo Fisher TSQ Quantum Access MAX mass spectrometer that was connected with a Dionex Ultimate 3000 Series Pump and WPS-3000 Autosampler (Thermo Fisher Scientific, Waltham, MA). Electrospray ionization (ESI) analysis in full scan mode was used to monitor each reaction in both positive and negative ion modes. These data were recorded using optimized parameters for the ESI source and MS as follows: spraying solvent, ACN; spray voltage +3.5 kV (positive mode) and −4.0 kV (negative mode); capillary temperature, 250° C.; Sheath gas pressure, 10 psi; scan time, 1 s; Q1 peak width (FWHM), 0.70 Th; micro scans, 3. The autosampler settings were as follows: MS acquire time, 2 min; sample injection volume, 10 µL. Thermo Fisher Xcalibur software was used to process the data from the MS spectrometer.

NMR Analysis $^1$H-NMR and $^{13}$C-NMR were acquired using a Bruker AV-III-500-HD NMR spectrometer (Billerica, Mass., USA). Samples for NMR were prepared by dissolving ~5 mg of sample in CDCl$_3$. MestReNova 10.0 software was used to analyze the $^1$H-NMR and $^{13}$C-NMR.

Chemtrix S1 Microfluidics System.

The two step synthesis of lomustine was performed using a Labtrix 51 microfluidic reactor system (Chemtrix, Ltd, Netherlands). The reactor parts are made of PPS (polyphenylsulfide) and perfluoroelastomer to provide excellent chemical resistance. The system has a temperature range for synthesis from −20° C. to +195° C. and pressures of up to 35 bar. The outer diameter of the fluorinated ethylene propylene (FEP) tube is 1/32 inches and the inner diameter is 150 µL. The 3223 and 3225 microreactors are made of glass and were used for all conducted reactions. The staggered orientated microreactor (SOR) chip 3223 (three inlets and one outlet, volume 10 µL) and 3225 (four inlets and one outlet, volume 10 µL) have a channel width of 300 µm and a channel depth of 120 µm. The Labtrix unit is able to independently pump five syringes into the microreactor seated on a Peltier heating and cooling unit. All the gastight glass syringes were bought separately from Hamilton Company (Hamilton, Reno, Nev.). The tubing and fittings connect the syringes with the selected connection port on the microreactor. All operations were controlled using a Chemtrix GUI software installed on a laptop that was connected to the Labtrix S1 casing with a USB cable.

Liquid-Liquid Separator.

All the liquid-liquid separations were performed using a SEP-10 unit (Zaiput Flow Technologies, Cambridge, Mass.). The separator uses a porous hydrophobic PTFE membrane (OB-900) which allows flow of the organic phase through the membrane. The organic phase wets the membrane while the aqueous phase does not. A built-in pressure controller is used to maintain the appropriate pressure differential that is required of the flow for both sides of the membrane.

DESI-MS Analysis

The DESI-MS evaluation was done following the previously published method of Wleklinski et al[1] except that the density of reaction spots was 1536 spots/plate instead of 6144/plate using reagents that were pipetted into standard polypropylene 384-well plates using a liquid handling robot (Biomek i7; Beckman-Coulter, US). DESI-MS slides were fabricated from porous PTFE sheets (EMD, Millipore Fluoropore, Saint-Gobain) glued onto a glass support (Foxx Life Sciences). The PTFE sheet was cut with scissors and bonded to the glass slides using spray adhesive (Scotch Spray mount). No signs of interference from the glue was observed. The reagents were mixed at 1:1 stoichiometry in various solvents (EtOAc, THF, DMSO, Toluene, ACN, DCM, EtOH and MeOH) and rhodamine B dye was added to some wells of the plate as a fiducial marker. After the reagents were mixed, 50 nL of the reactions were deposited onto a porous PTFE surface at 1,536 spot density using a magnetic pin tool equipped with slotted transfer pins. DESI-MS data was acquired using a linear ion trap mass spectrometer (LTQ XL; Thermo Scientific, San Jose, Calif.) equipped with a commercial DESI-imaging source (DESI 2D source, Prosolia Inc., Indianapolis, Ind.). The instrument was controlled using Xcalibur v. 4.0 software to run worklists for DESI-MS data acquisition. The DESI spray angle was 55° using MeOH as spray solvent, and with an applied voltage of 5 kV. Mass spectra were acquired at the positive ion mode over the m/z range of 50-500. The DESI-MS imaging lateral resolution was 350 μm. This was achieved using stage speed of 4,376 μm/sec and the instrument scan time of 80 ms. For data processing, data were visualized using an in-house software designed[1] to automatically search for the m/z values of reactants, intermediates, and lomustine fragments to generate a YES/NO visualization output for each spot in the PTFE plate imaged by DESI-MS. Data files also were combined into .img files using Firefly software (Prosolia Inc., Indianapolis, Ind.). Ion images were plotted using BioMAP (Novartis, freeware). The expected m/z values for the lomustine fragments were plotted and visualized using the BioMAP rainbow false color scale where the minimum and maximum ion intensity values were set to the best contrast for each ion.

HPLC-MS Analysis

HPLC/MS analysis was performed using an Agilent 6545 UPLC/quadrupole time-of-flight (Q-TOF) mass spectrometer (Palo Alto, Calif.), with an Agilent XDB-C18 column (3.5 μm, 150×2.1 mm i.d.) and 5 μL injection volume. A binary mobile phase, consisting of solvent systems A and B was used. A was 0.1% formic acid (v/v) in ddH$_2$O and B was 0.1% formic acid (v/v) in ACN. Isocratic elution of A:B at 95:5 was used, with a column flow rate of 0.3 mL/min. Following the separation, the column effluent was introduced by positive mode electrospray ionization (ESI) into the mass spectrometer. High mass accuracy spectra were collected between 70-1000 m/z. Mass accuracy was improved by continuously infusing Agilent Reference Mass Correction Solution (G1969-85001). The MS detection conditions were: ESI capillary voltage, 3.5 kV; nebulizer gas pressure, 30 psig; gas temperature, 325° C.; drying gas flow rate, 8.0 L/min; fragmentor voltage, 130 V; skimmer, 45 V; and OCT RF V, 750 V.

Carbamylation of Cyclohexylamine

Experimentation.

A solution of cyclohexylamine (1, 500 mmol, 1 equiv) in THF was loaded into 1 mL Hamilton gas tight glass syringe. Triethylamine (TEA) (500 mmol, 1 equiv) and 1-chloro-2-isocyanatoethane (2, 700 mmol, 1.4 equiv) solutions in THF were individually loaded into another two 1 mL Hamilton gas tight glass syringes. Each solution was simultaneously dispensed into the SOR 3225 reactor to engage the reactants. The syringe containing 2 was protected from light by covering it with aluminum foil. The reactions were run at 25° C., 50° C. and 65° C. at residence times of 10 sec, 30 sec, 60 sec and 180 sec. The reactions were monitored by TLC and ESI-MS. Product 3 was collected after evaporation and washing with cold Et2O. The white solid product was stored in the dark at 4° C. Any clogged chips or tubing of the setup was cleaned using THF and EtOH. The subsequent TLC, ESI-MS, MS/MS and NMR ($^1$H and $^{13}$C) analyses were performed after purification.

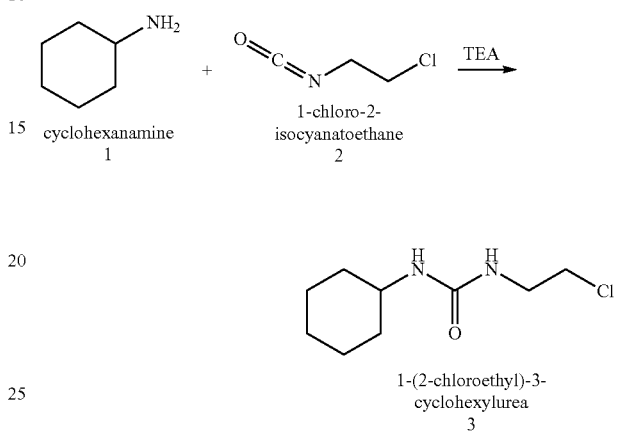

Scheme S1: Synthesis of 3 in flow

NMR $^1$H NMR (500 MHz, CDCl$_3$, ppm): δ$_H$=4.84 (t, J=5.85, 1 H), 4.42 (d, J=7.35 Hz, 1 H), 3.62 (t, J=5.60Hz, 2 H), 3.54 (t, J=5.70Hz, 2 H), 3.51-3.45 (m, 1 H), 1.95-1.92 (m, 2 H), 1.72-1.67 (m, 2 H), 1.62-1.58 (m, 1 H), 1.39-1.30 (m, 2 H), 1.19-1.06 (m, 3 H); $^{13}$C NMR (500 MHz, CDCl$_3$, ppm): δ$_c$=157.04, 49.29, 45.25, 42.12, 33.88, 25.57, 24.9

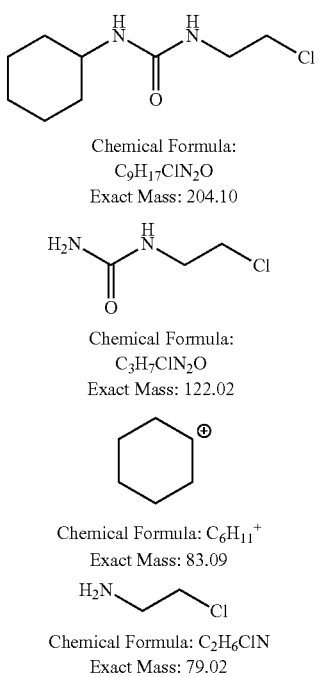

Scheme S2: Fragments from 1-(2-chloroethyl)-3-cyclohexylurea, 3

ESI-MS (m/z): 205/207 (M+H$^+$), 227/229 (M+Na$^+$), 408/410 (2M$^+$).

ESI-MS/MS of m/z 205: 205 (M+H$^+$), 123 (C$_3$H$_7$ClN$_2$O+H$^+$), 83 (C$_6$H$_{11}^+$) (80 (C$_2$H$_6$ClN$^+$)

Figure 8A:
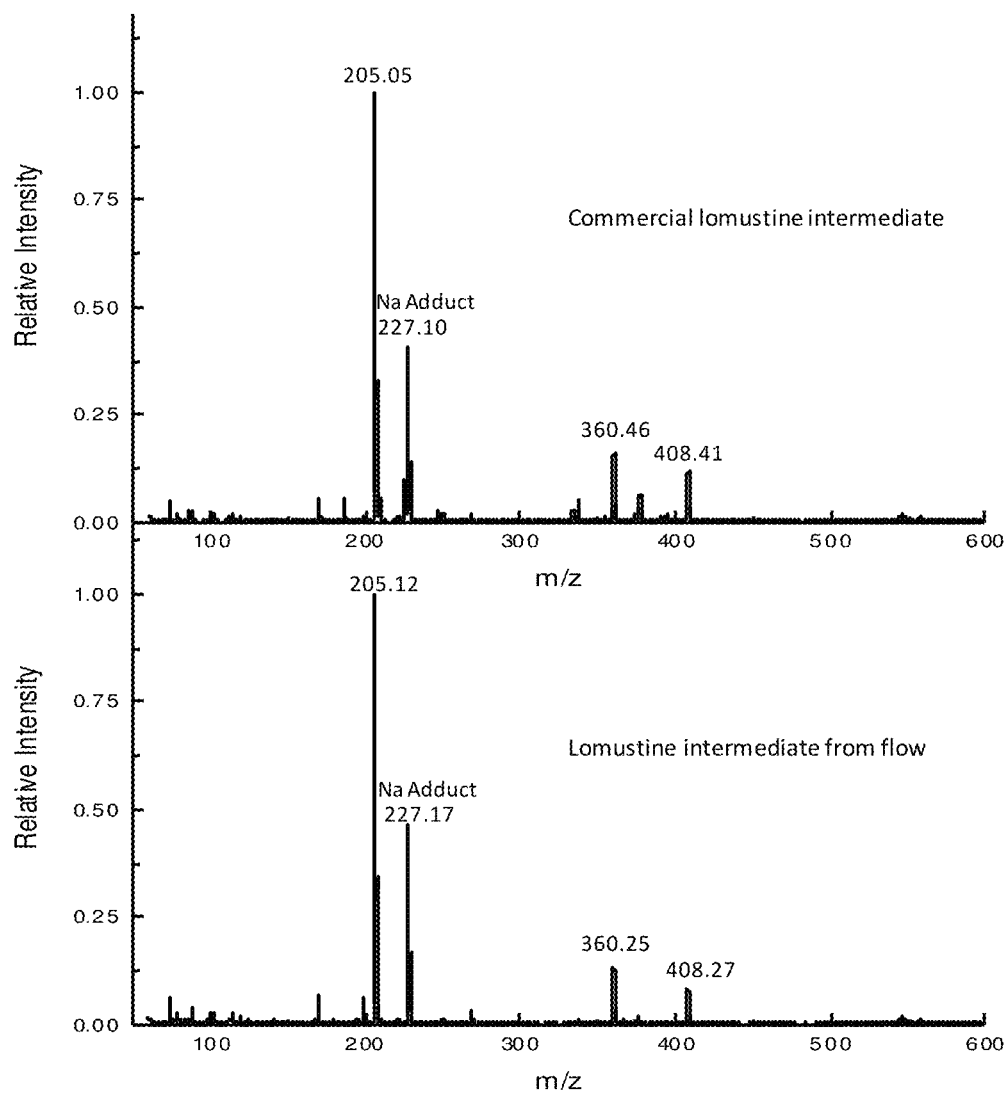
FIG. 8A and FIG. 8B: Full ESI-MS scan and MS/MS of commercially available 3 and synthesized 3 derived from flow under the reaction conditions of 50° C., 1 min.
Figure 8B:
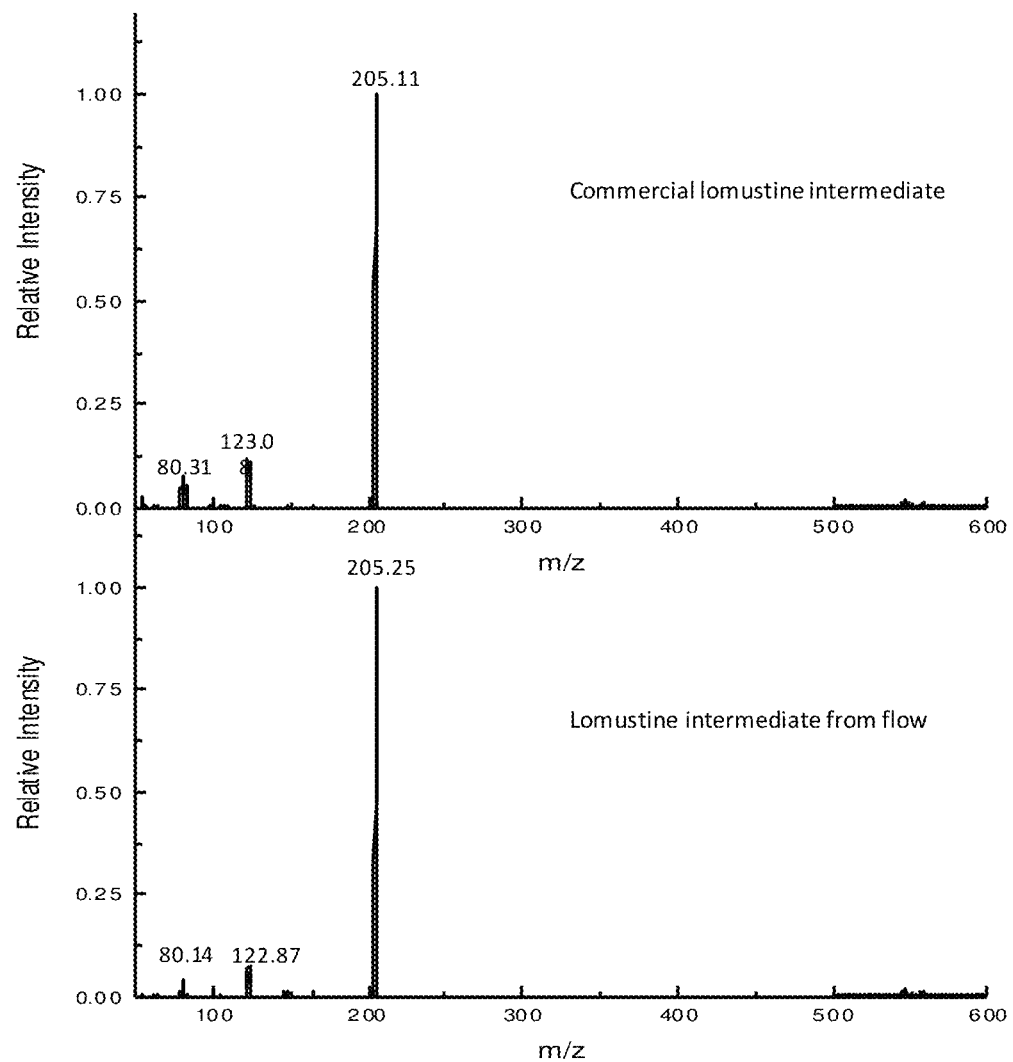

Full ESI-MS scan and MS/MS of commercially available 3 and synthesized 3 derived from flow under the reaction conditions of 50° C., 1 min are shown in FIG. 8A and FIG. 8B.

DESI-MS Screening.

Preparation of Reaction (Master) Plates and Stamping on DESI-MS Slides.

Stock solutions of 3 and nitrosation reagents were made at 4 different concentrations (50, 100, 150, 200 mmol) in THF and ACN. Each reagent solution was also prepared (0.1 M) in eight different solvents ((EtOAc, THF, DMSO, Toluene, ACN, DCM, EtOH and MeOH). At first, 20 µL of 3 solution was dispensed into a 384-well master plate and then the corresponding nitrosation reagents added to the plate in a stoichiometry 1:1 using a Beckman i7 liquid handling robot, resulting in a final volume of 40 µL in each well. Moreover, a master plate was made using only commercially available 3 and lomustine to compare the data. Rhodamine was dissolved in acetonitrile (0.25 mg/mL) and transferred to a reservoir. A pin tool fitted with 50 nL pins was used to transfer solutions from the master plates as well as from the Rhodamine reservoir onto the DESI-MS substrates. The master plate was pinned three times in separate locations with reaction mixtures and Rhodamine once, resulting in 1536 density on the microtiter plate used as the DESI-MS substrate.

Figure 9:
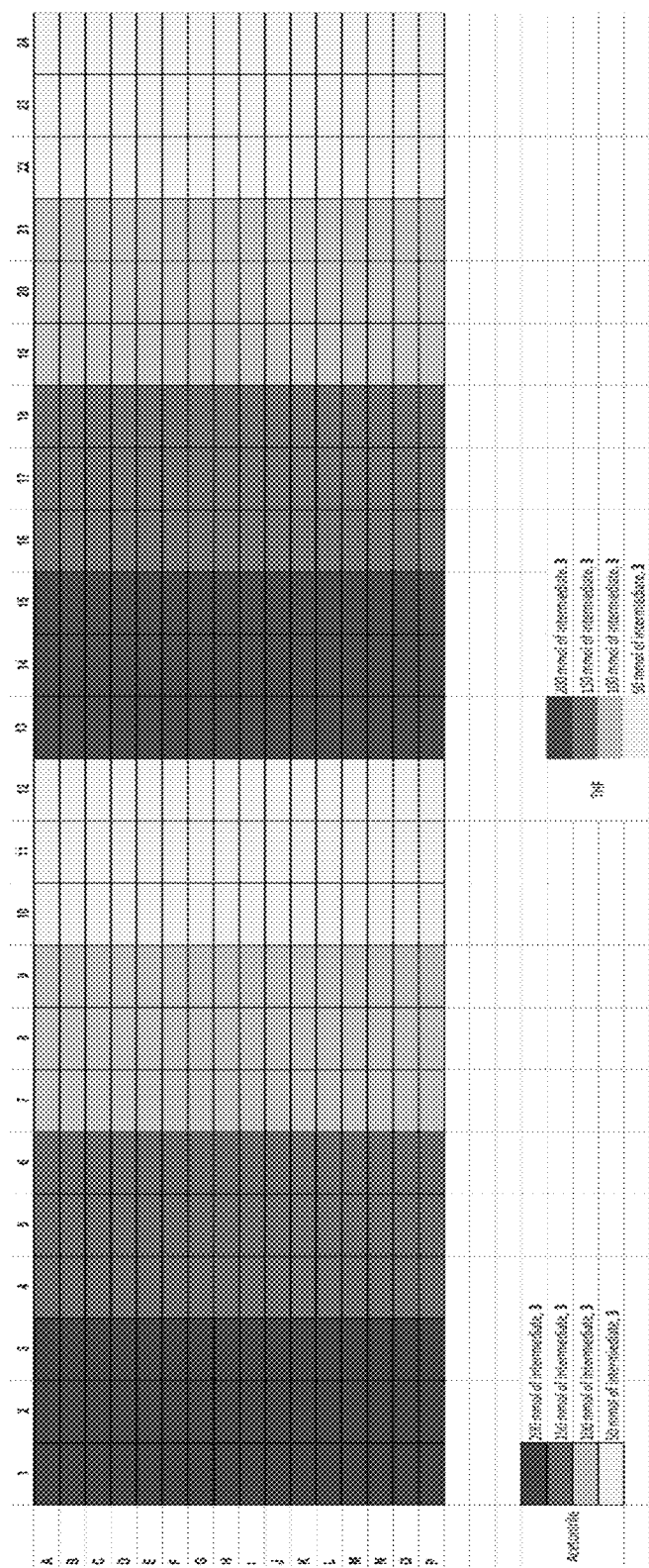
FIG. 9: DESI master plate layout using four different concentrations in two solvents.
Figure 10:
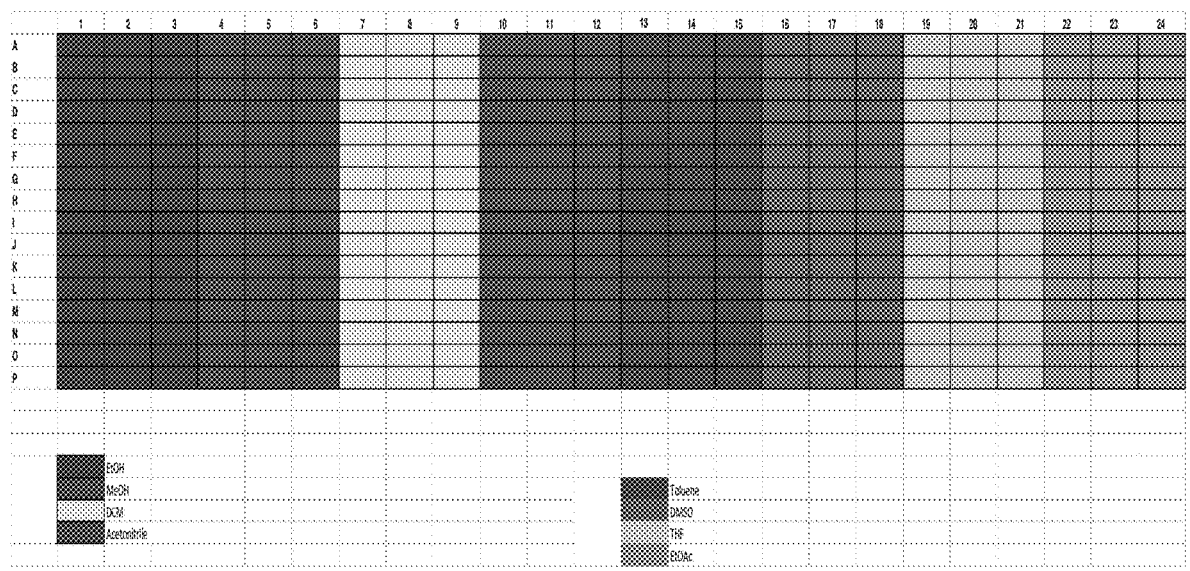
FIG. 10: DESI master plate layout using eight different solvents.
Figure 11:
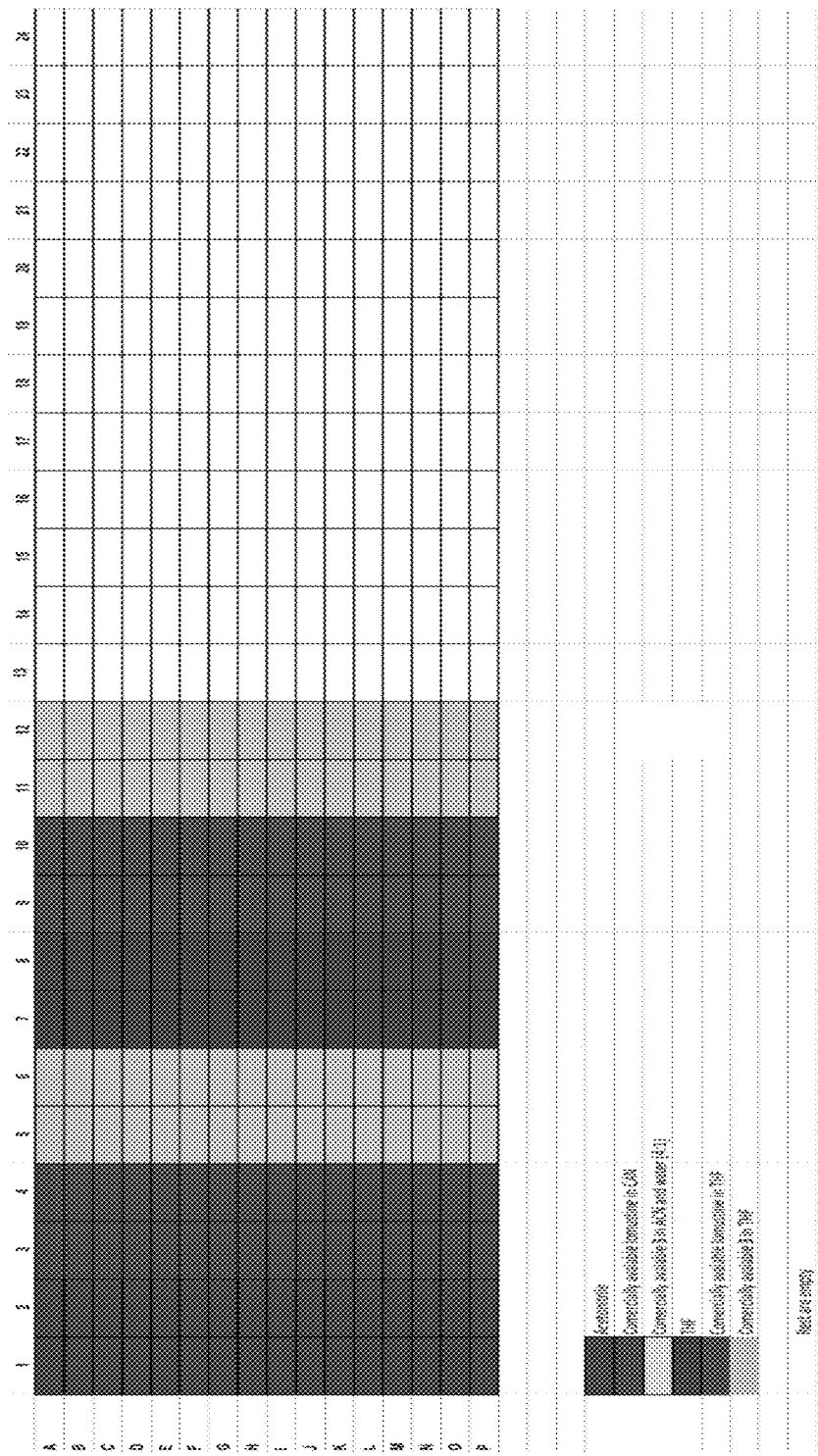
FIG. 11: DESI master plate layout using only commercially available 3 and lomustine.
Figure 12:
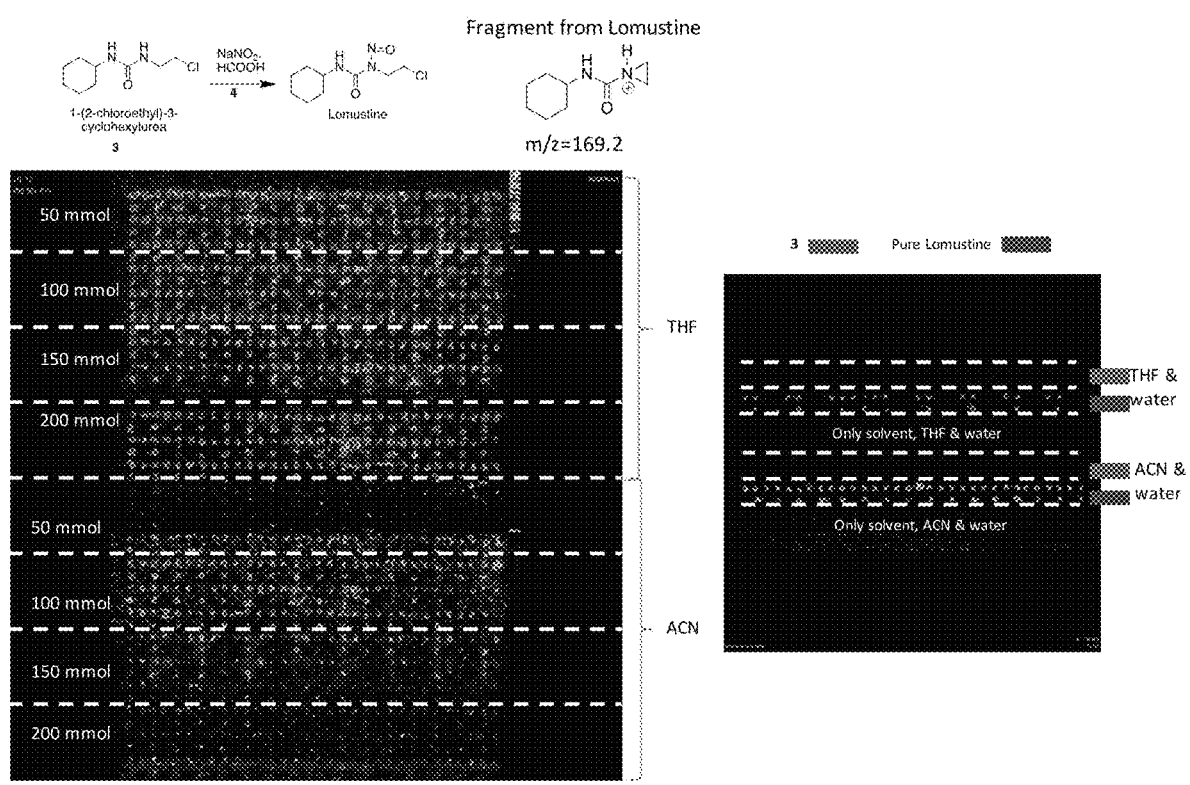
FIG. 12: (left) Direct DESI-MS data comparison between the two nitrosation reactions in THF and ACN in different concentration. (right) DESI-MS data of commercially available 3 and lomustine standards. The data was analyzed using BioMAP imaging software.
Figure 13:
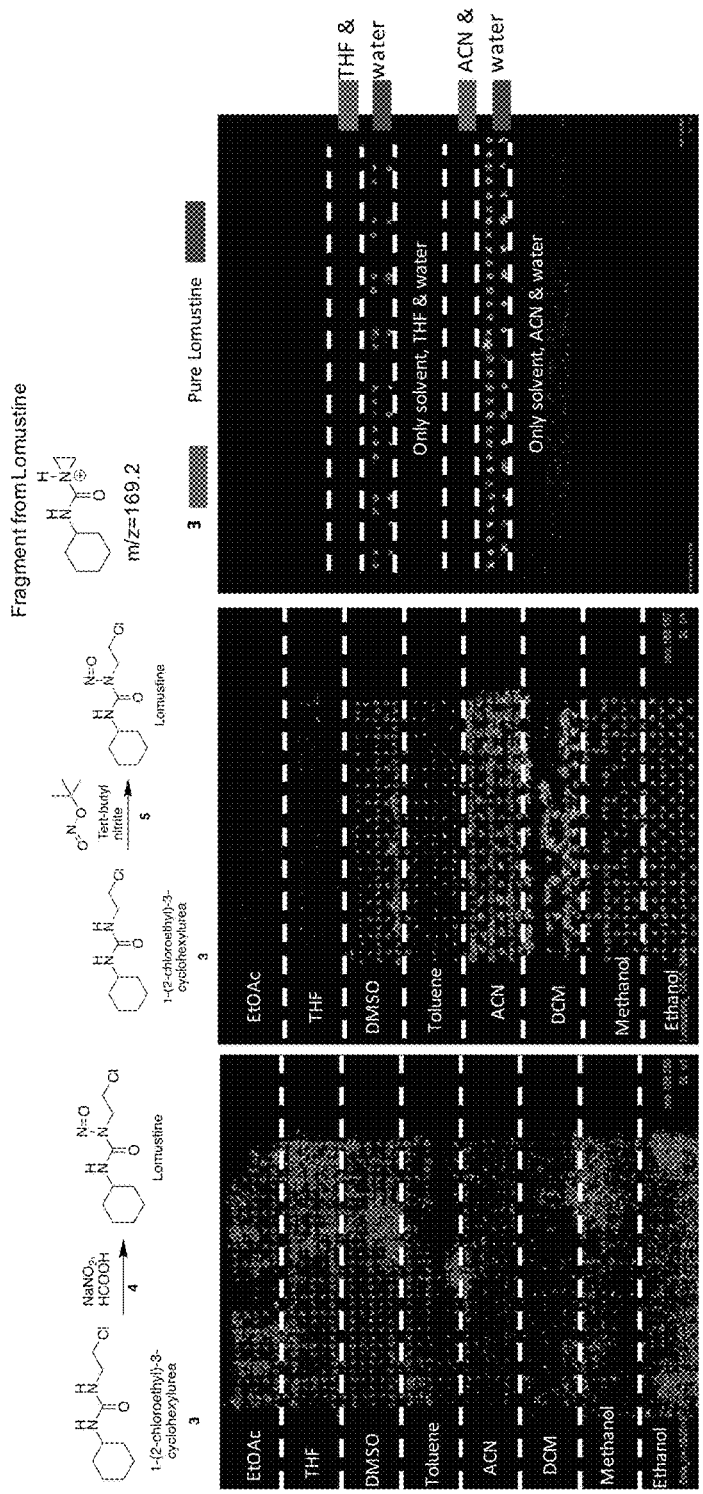
FIG. 13: (left & center) Direct DESI-MS data comparison between the two nitrosation reactions in different solvents. (right) DESI-MS data of commercially available 3 and lomustine standards. The data was analyzed using BioMAP imaging software.
Figure 14A:
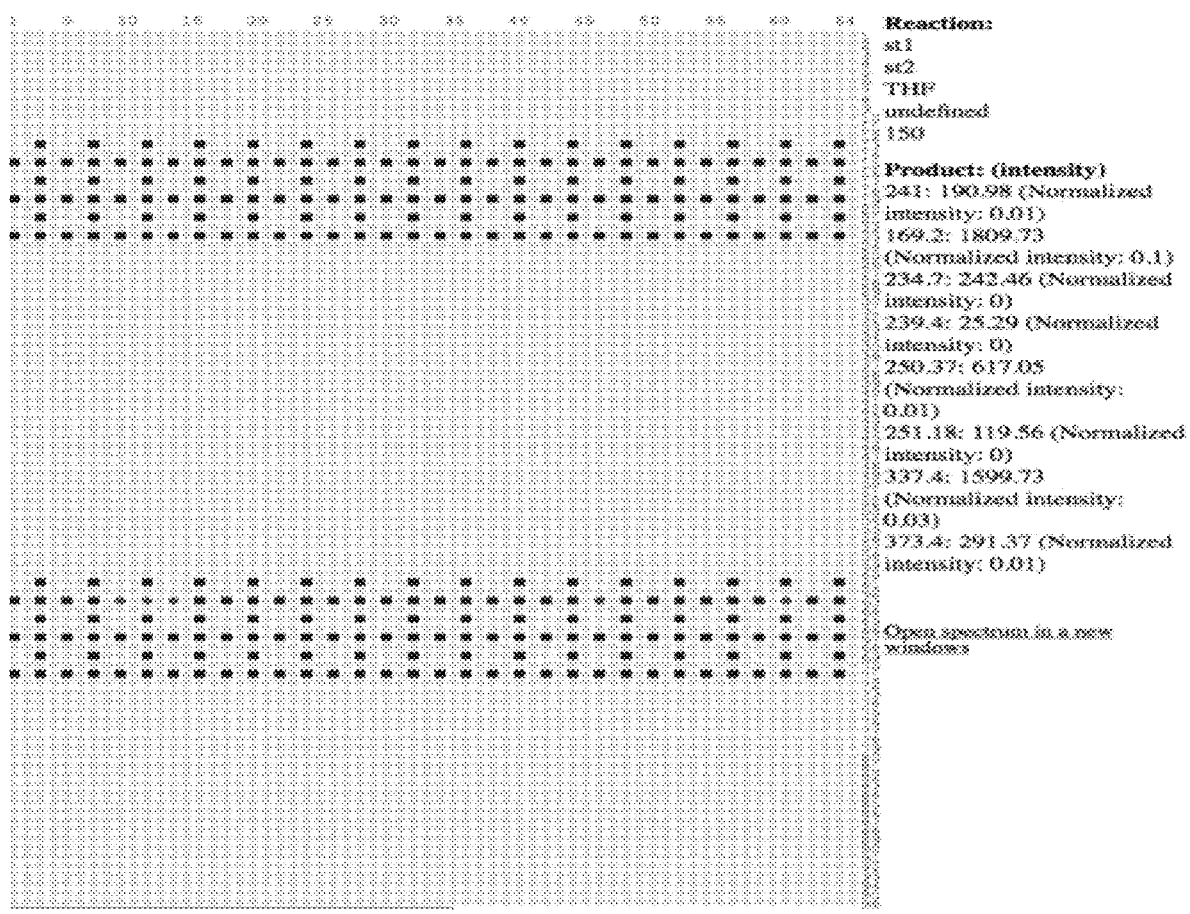
FIG. 14A to FIG. 14C: Map of the DESI-MS plates showing some of the expected ions where the nitrosation reaction was screened using different stoichiometries as well as commercially available standards. Green dots indicate the presence of the m/z expected for the reaction product (successful reaction), Red dots indicate that the expected m/z for the reaction product was not present at the reaction spot (unsuccessful reaction condition). A: NaNO₂, concentration screening using the lomustine ion (m/z 169) intensity; B: NaNO₂, solvent screening using the lomustine ion (m/z 169) intensity; C: TBN, solvent screening using the lomustine ion (m/z 169) intensity
Figure 14B:
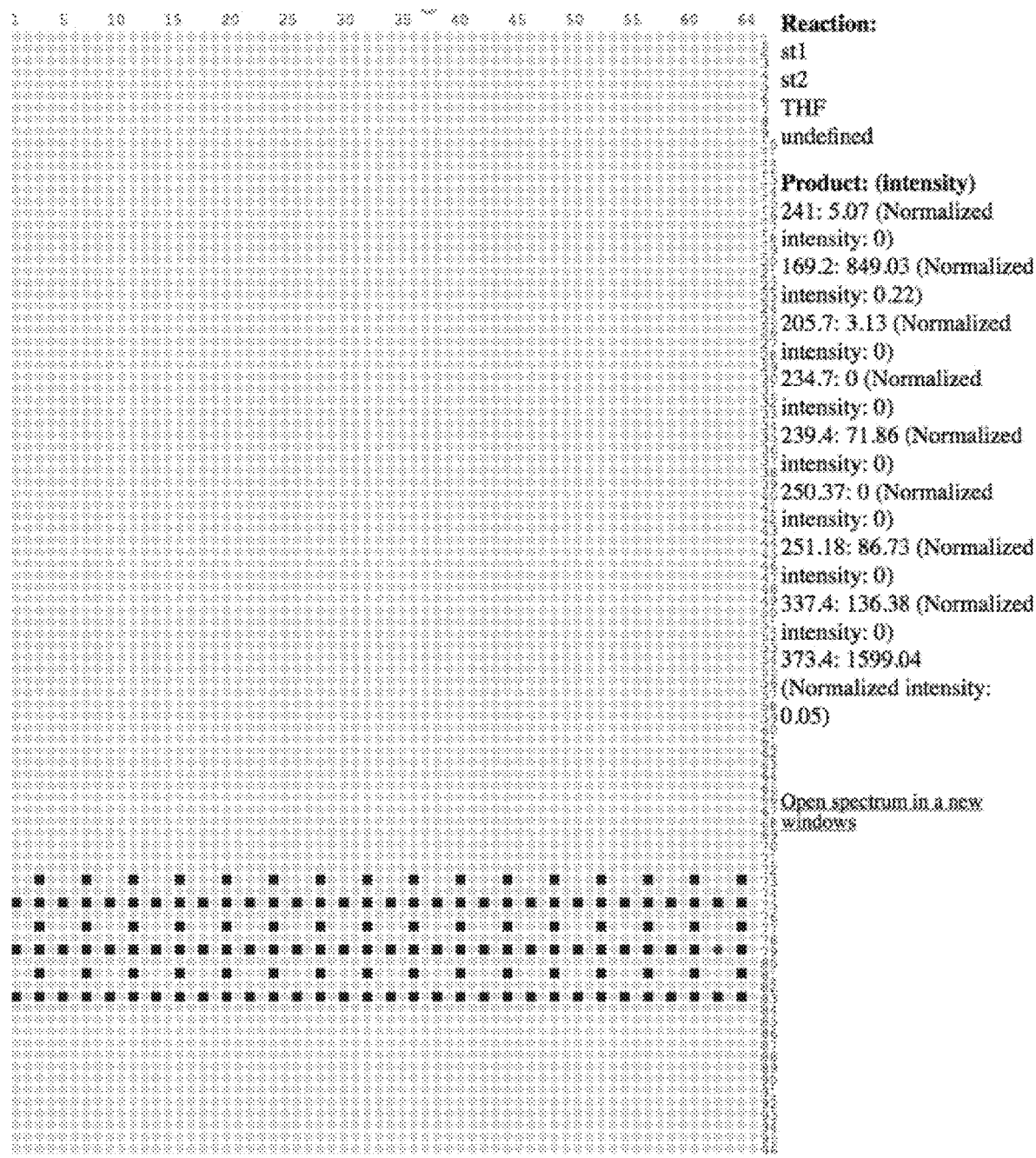
Figure 14C:
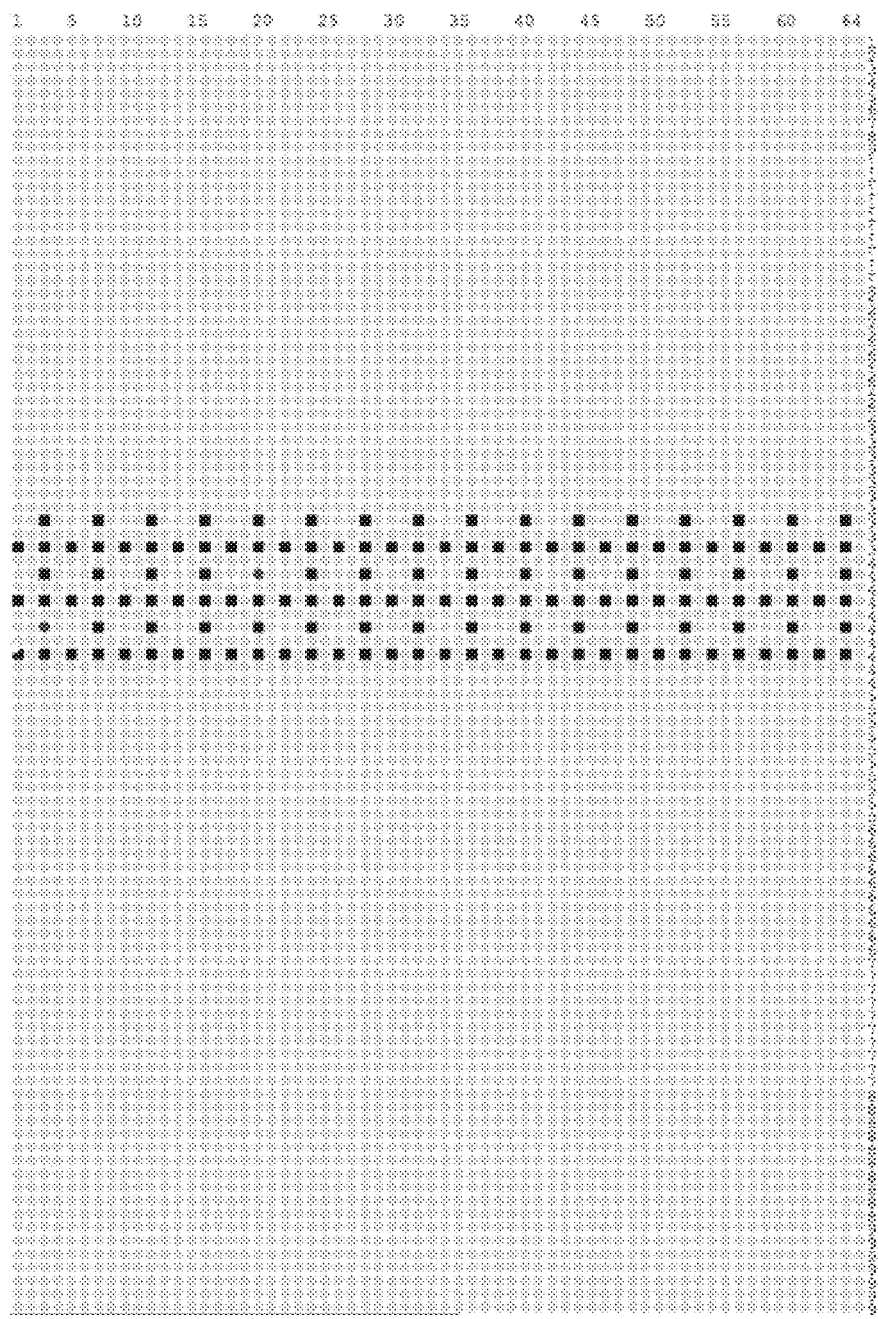
Figure 15:
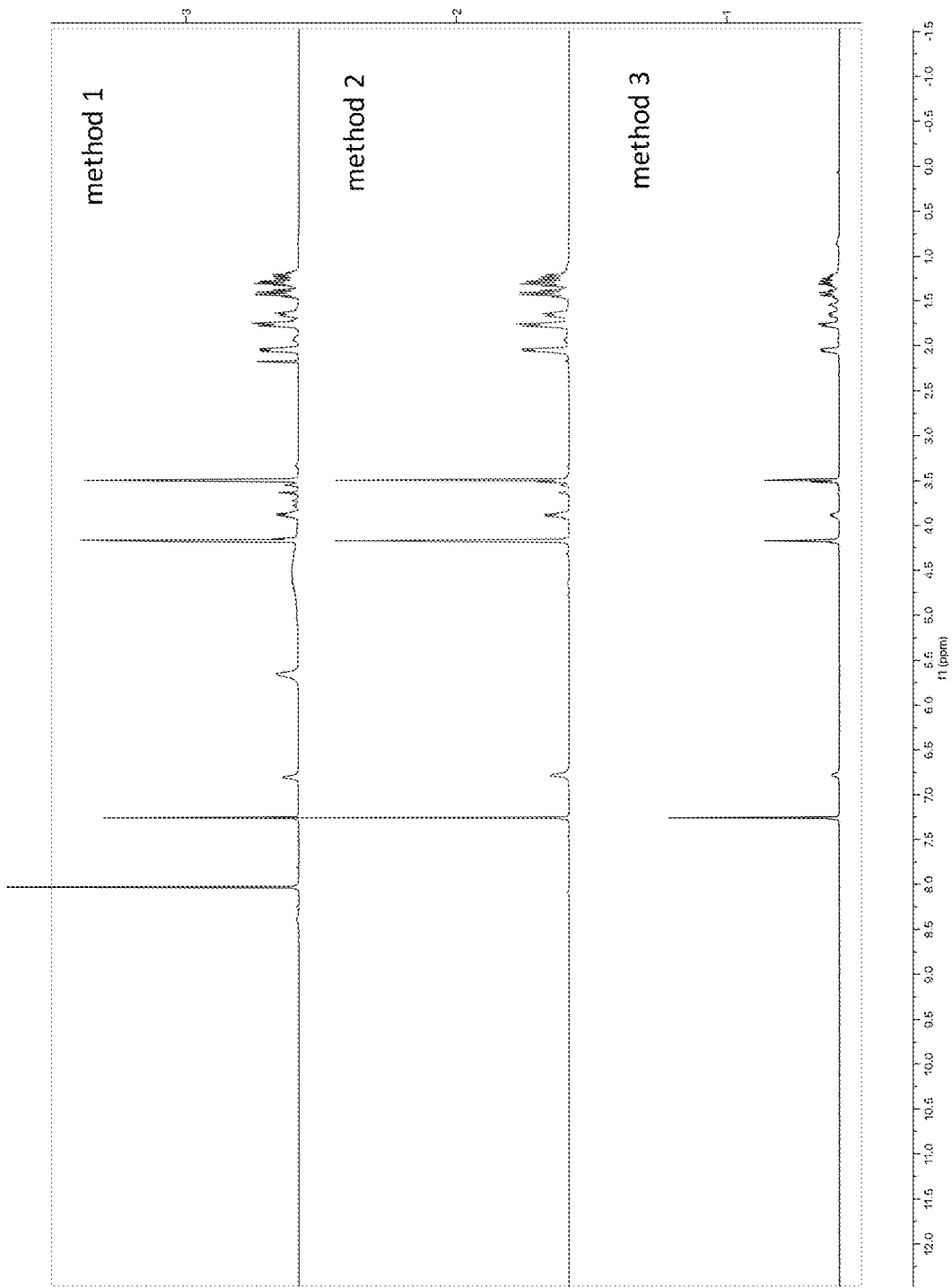
FIG. 15: Comparison of ¹H NMR of lomustine synthesized by continuous flow for different methods of purification.
Figure 16:
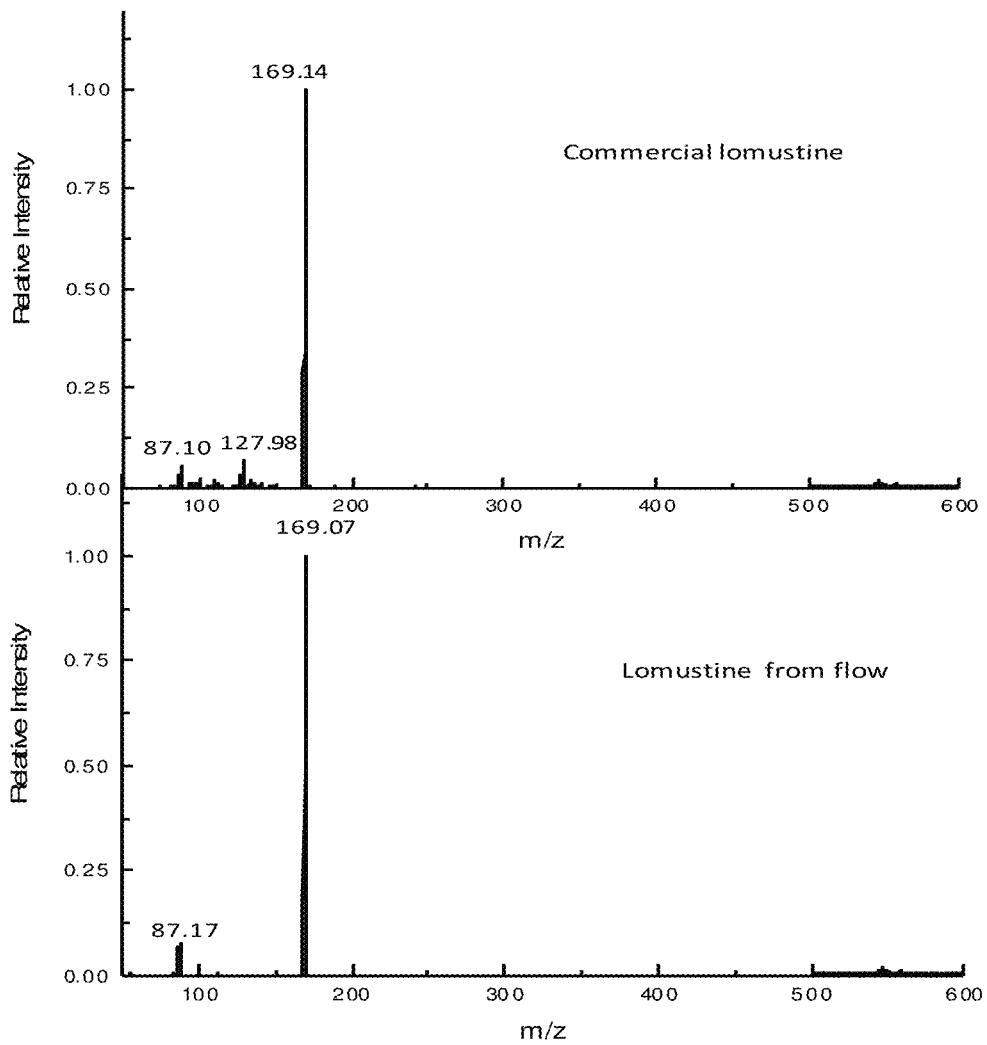
FIG. 16: Full MS scan and MS/MS of m/z=169 from commercially available lomustine and synthesized lomustine form flow. Reaction conditions were 25° C., 8 min.

DESI-MS Outline is shown in FIGS. 9-11

Nitrosation of 1-(2-chloroethyl)-3-cyclohexylurea, 3.

Experimentation.

A solution of 3 (245 mmol, 1 equiv) in 98% formic acid was loaded into a 1 mL Hamilton gas tight glass syringe. NaNO$_2$ (735 mmol, 3 equiv) solution in MeOH:H$_2$O (4:1) was separately loaded into another 1 mL Hamilton gas tight glass syringe and dispensed into the SOR 3225 reactor to engage the reactants. The reactions were run at 0° C. at residence times of 30 sec, 1 min, 3 min, 5 min, 8 min, and 10 min. For nitrosation with 5, a solution of 3 in ACN:EtOH (3.7:1) (200 mmol, 1 equiv) and 5 in ACN (600 mmol, 3 equiv, protected from light by covering the syringe with aluminum foil) were loaded into two separate 1 mL Hamilton gas tight glass syringes and dispensed into the SOR 3223 reactor. All the reactions were monitored at two different temperatures (50° C. and 25° C.) at residence times of 30 sec, 1 min, 3 min, 5 min, 8 min, and 10 min. Reaction progress was monitored by TLC and ESI-MS. The reaction mixtures were extracted by Et$_2$O, evaporated, and dried over anhydrous Na$_2$SO$_4$. The crude oily product was purified by dissolving it in hot petroleum ether, hot filtering the solution, and evaporating the filtrate to dryness in vaccuo to give the yellowish solid lomustine that was stored at −20° C. TLC, ESI-MS, MS/MS, NMR ($^1$H and $^{13}$C), and yield analyses were performed after purification Three purification methods were examined to purify the compounds as described in the main manuscript. The NMR spectra for the different purification methods are shown here for comparison.

ESI-MS:

Scheme S3: Fragments of lomustine in MS

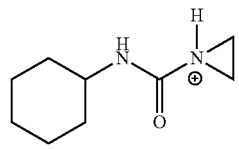

Chemical Formula:
C$_9$H$_{17}$N$_2$O$^+$

Exact Mass: 169.13

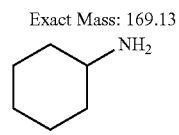

Chemical Formula:
C$_6$H$_{13}$N
Exact Mass: 99.10

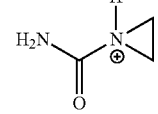

Chemical Formula: C$_3$H$_7$N$_2$O$^+$
Exact Mass: 87.06

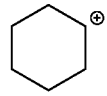

Chemical Formula: C$_6$H$_{11}^+$
Exact Mass: 83.09

ESI-MS (m/z): 169 (C$_9$H$_{17}$N$_2$O$^+$), 100 (C$_6$H$_{13}$N+H$^+$), 87(C$_3$H$_7$N$_2$O$^+$), 83 (C$_6$H$_{11}^+$)

ESI-MS/MS of m/z 169: 169 (C$_9$H$_{17}$N$_2$O$^+$), 100 (C$_6$H$_{13}$N+H$^+$), 87(C$_3$H$_7$N$_2$O$^+$)

Telescopped Synthesis of Lomustine Reactors.

For scale up and telescoping of the two steps, fluorinated ethylene propylene (FEP) tubing was used. The outer diameter of the FEP tube was 1/16 inches and the inner diameter is 0.8 mm. The first reactor volume was 5 µL and the second reactor volume was 100 µL.

Experimentation.

Figure 17:
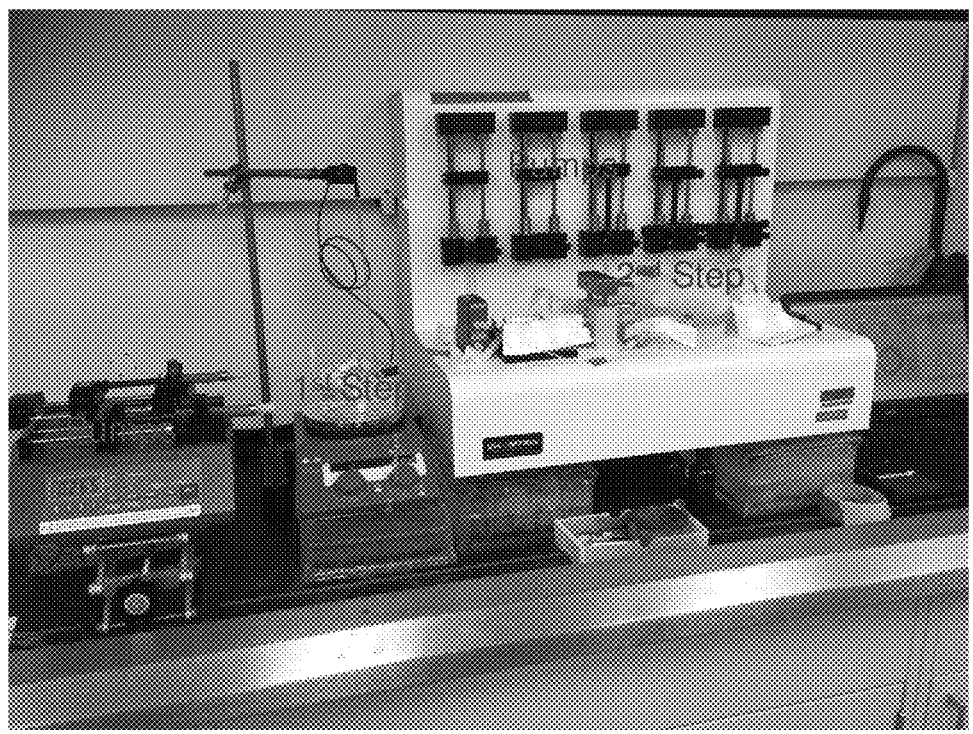
FIG. 17: Telescoped two step synthesis of lomustine using sodium nitrite in the second step.
Figure 18:
FIG. 18: First step of the telescoped synthesis of lomustine.
Figure 19:
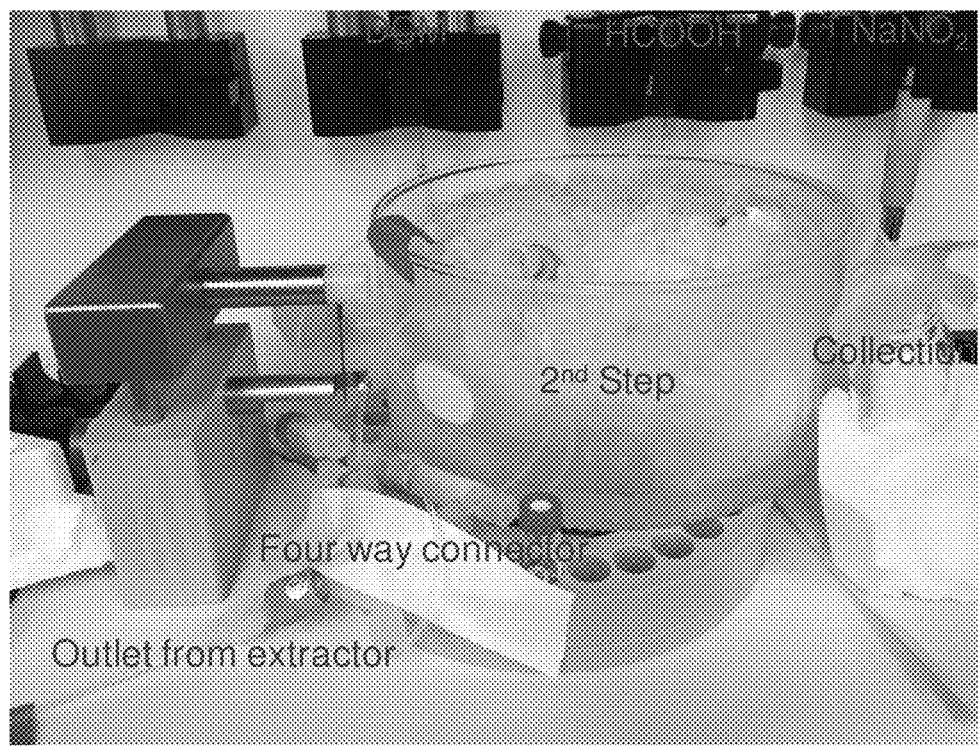
FIG. 19: Second step of the telescoped synthesis of lomustine using NaNO₂ as a nitrosation reagent.
Figure 20:
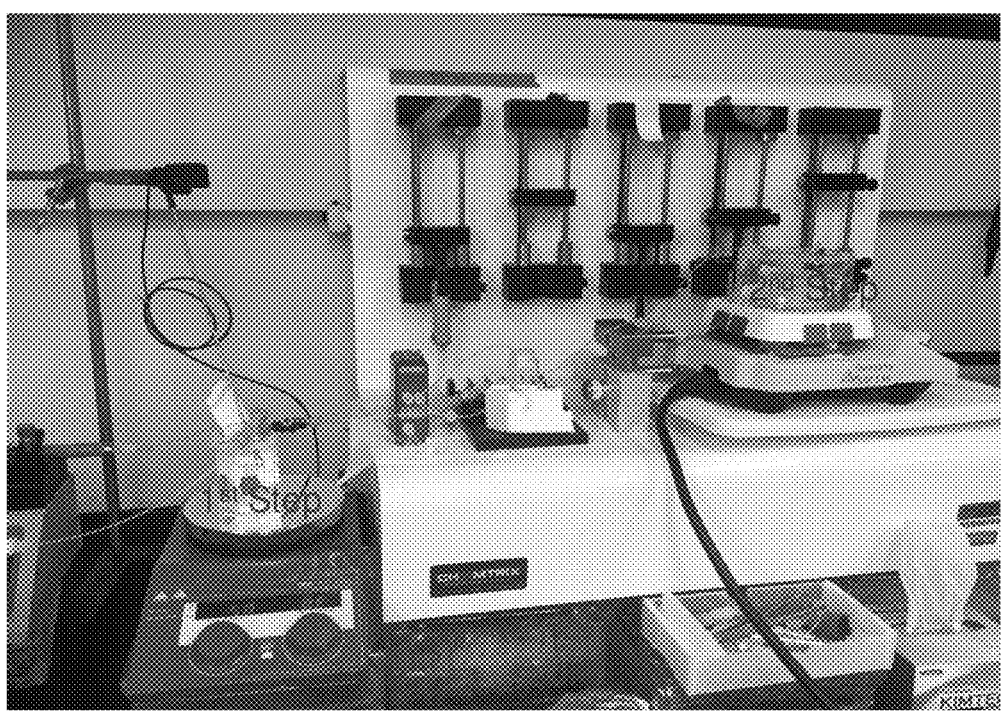
FIG. 20: Telescoped lomustine synthesis using TBN as a nitrosation reagent, before reaction initiation.
Figure 21:
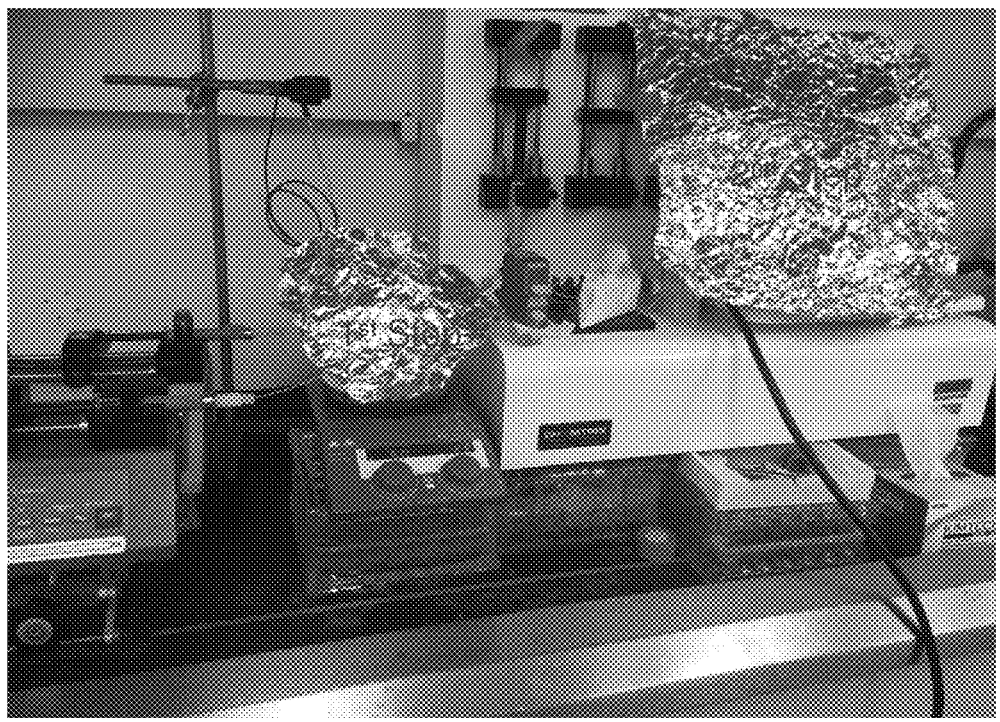
FIG. 21: Telescoped lomustine synthesis using TBN (protected from light).
Figure 22:
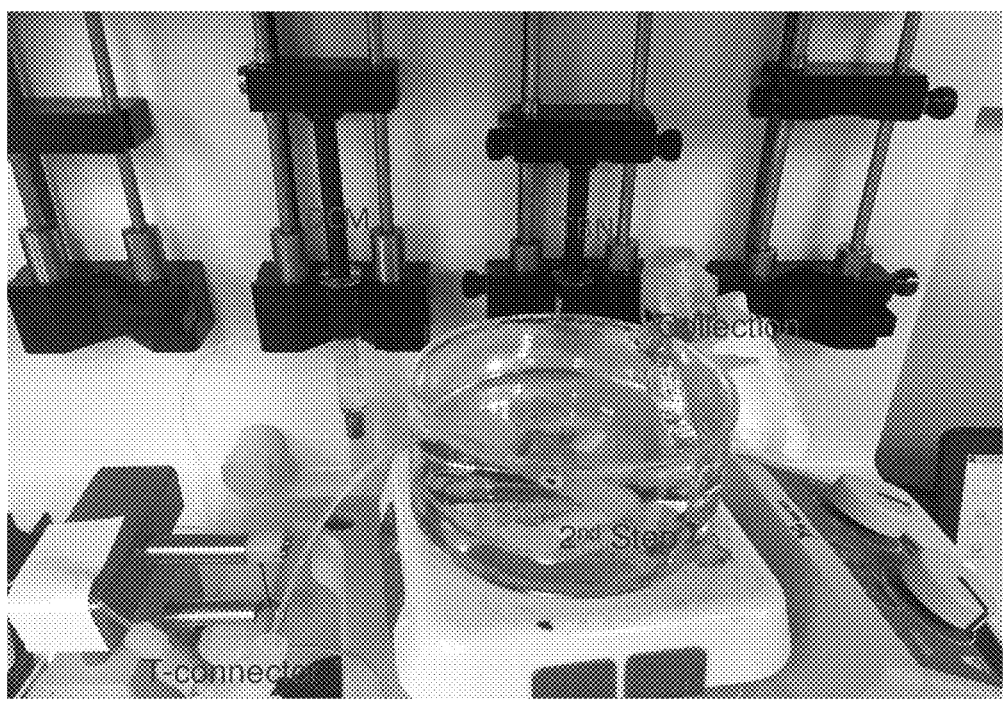
FIG. 22: Second step of the telescoped synthesis of lomustine using TBN.
Figure 23:
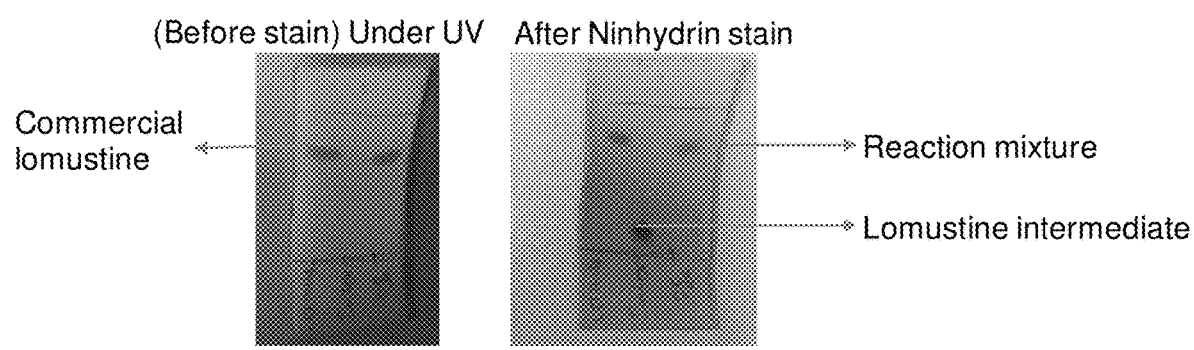
FIG. 23: TLC monitoring during lomustine synthesis in flow
Figure 24:
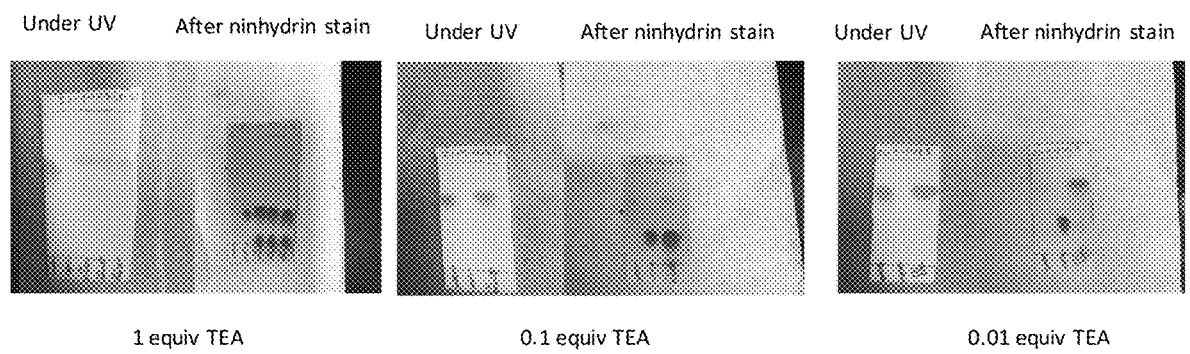
FIG. 24: Comparison of TLC of telescoped lomustine synthesis using different equivalents of base

Cyclohexaneamine, 1 (1 M, 1 equiv) and triethylamine (0.01 M, 0.01 equiv) were prepared in DCM separately. Next, the two separate solutions were mixed in a 1:1 (v:v) ratio and loaded into a 5 mL Hamilton gastight syringe. Then, a solution of 1-chloro-2-isocyanatoethane, 2 (0.7 M) was prepared in THF and loaded into a 5 mL Hamilton gastight syringe that was covered with aluminum-tape for light protection since it is light sensitive. The two syringes were connected to a T-connection and outlet of the T-connector was connected to the first tubing reactor using microtubes, check valves and other connectors (FIG. 17 and FIG. 18). The setup for producing 3 was assembled and placed in a heated H$_2$O bath that was maintained at 50° C. The outlet of the tube-reactor was connected to a four-way connector, where two of the outlets of the connectors were connected to a 10 mL Hamilton gastight syringe containing H$_2$O and a 5 mL Hamilton gastight syringe containing DCM. The four-way connector provide sufficient mixing for the extraction of the triethylamine base in the aqueous phase and leaving 3 in the organic phase. The fourth outlet was connected to the liquid-liquid separator (SEP-10) in which the DCM passes through the membrane carrying with it 3 to the next reaction step. The outlet of the aqueous phase from the separator was connected to a waste vial. For using sodium nitrite as a nitrosation reagent, the outlet of the organic phase was connected to a four-way connector. Sodium nitrite, 4 (1.5 M, 3 equiv) solution in THF and formic acid were loaded into two separate 5 mL Hamilton gastight syringes and connected to the a four-way connector. The outlet of the four-way connector is connected to the second tubing reactor. When using TBN, 5 as a nitrosation reagent, we doubled the concentration of the starting material. The outlet of the organic phase from liquid-liquid extractor was connected to a T-connector, where one outlet was connected to a 5 mL Hamilton gastight syringe containing tert-Butyl nitrite, 5 (5 M) in ACN. The outlet of the T-connector was connected to the second tubing reactor. The second reactor was placed in a $H_2O$ bath with a constant temperature of 25° C. and the outlet of this reactor was connected to a collection vial. The reactions were monitored by TLC and ESI-MS. The purification and analyses were conducted as described above, except that HPLC-MS analysis was performed to evaluate the purity of the product.

TLC and Purification. Reaction progress was monitored by TLC using 1:1 EtOAc:Hexanes as eluent. Lomustine was visualized under shortwave UV light (230 nm), while 3 was observed after staining with ninhydrin solution and heating. The extraction and purification was conducted by taking 500 µL from the collection vial and washing it with 2 mL of $H_2O$ and 2 mL of $Et_2O$ and extracted three times. The combined organic layers were dried using anhydrous $NaSO_4$. The $Et_2O$ was evaporated and the yellowish oil/solid was dissolved in hot petroleum ether, hot filtered, and the filtrate was removed under vacuum. The resulting solid was recrystallized from petroleum ether.

NMR $^1$H NMR (500 MHz, $CDCl_3$, ppm): $\delta_H$=6.78 (s, 1H), 4.18 (t, J=7.5, 2 H), 3.92-3.84 (m, 1H), 3.50 (t, J=7.5 Hz, 2 H), 2.07-2.04 (m, 2 H), 1.79-1.75 (m, 2 H), 1.68-1.63 (m, 1 H), 1.45-1.39 (m, 2 H), 1.32-1.24 (m, 3 H); $^{13}$C NMR (500 MHz, $CDCl_3$, ppm): $\delta_C$=151.78, 49.98, 40.03, 38.89, 33.09, 25.39, 24.76

Proton NMR of lomustine from flow synthesis, or Carbon NMR of lomustine, 6 from flow synthesis are available. Comparison of Proton NMR of lomustine, 6 in flow synthesis with commercially available lomustine, 6, and comparison of carbon NMR of lomustine, 6 in flow synthesis with commercially available lomustine, 6 are available upon request.

HPLC/MS-MS Analysis

HPLC/MS analysis was performed on an Agilent 6545 UPLC/quadrupole time-of-flight (Q-TOF) mass spectrometer (Palo Alto, Calif.), with an Agilent XDB-C18 column (3.5 µm, 150×2.1 mm i.d) and 5 uL injection volume. A binary mobile phase consisting of solvent systems A and B were used. A was 0.1% formic acid (v/v) in dd$H_2O$ and B was 0.1% formic acid (v/v) in acetonitrile. Isocratic elution of A:B at 95:5 was used, with a column flow rate of 0.3 mL/min. Following the separation, the column effluent was introduced by positive mode electrospray ionization (ESI) into the mass spectrometer. High mass accuracy spectra was collected between 70-1000 m/z. Mass accuracy was improved by continuously infusing Agilent Reference Mass Correction Solution (G1969-85001). ESI capillary voltage was 3.5 kV, nebulizer gas pressure was 30 psig, gas temperature was 325° C., drying gas flow rate was 8.0 L/min, fragmentor voltage was 130 V, skimmer was 45 V, and OCT RF V was 750 V.

Full MS from HPLC-MS/MS and comparison between synthesized lomustine and commercially available lomustine are available upon request.

Flow Rates:

Flow Rates for $1^{st}$ step Reaction in Labtrix S1 system:

Chemtrix reactor chip: 3225, 10 µL, pressure: ambient pressure

| R1 Cyclohexane amine, 1 µL/min | R2 Triethylamine µL/min | R3 2-Chloroethyl isocyanate, 2 µL/min | Residence Time in min | Temperature ° C. |
|---|---|---|---|---|
| 20 | 20 | 20 | 0.167 | 50 |
| 6.67 | 6.67 | 6.67 | 0.5 | 50 |
| 3.33 | 3.33 | 3.33 | 1 | 50 |
| 1.11 | 1.11 | 1.11 | 3 | 50 |
| 0.67 | 0.67 | 0.67 | 5 | 50 |
| 0.417 | 0.417 | 0.417 | 8 | 50 |
| 0.333 | 0.333 | 0.333 | 10 | 50 |

Flow Rates for $2^{nd}$ step Reaction using $NaNO_2/HCO_2H$, 4 in Labtrix S1 system: Chemtrix reactor chip: 3225, 10 µL, pressure: ambient pressure

| R1 3 µL/min | R2 Sodium Nitrite µL/min | R3 Formic Acid µL/min | Residence Time in min | Temperature ° C. |
|---|---|---|---|---|
| 6.67 | 6.67 | 6.67 | 0.5 | 0 |
| 3.33 | 3.33 | 3.33 | 1 | 0 |
| 1.11 | 1.11 | 1.11 | 3 | 0 |
| 0.67 | 0.67 | 0.67 | 5 | 0 |
| 0.417 | 0.417 | 0.417 | 8 | 0 |
| 0.333 | 0.333 | 0.333 | 10 | 0 |

Flow Rates for $2^{nd}$ step Reaction using TBN, 5 in Labtrix S1 system. Chemtrix reactor chip: 3223, 10 µL, pressure: ambient pressure

| R1 3 µL/min | R2 tert-Butyl nitrite µL/min | Residence Time in min | Temperature ° C. |
|---|---|---|---|
| 10 | 10 | 0.5 | 50 |
| 5 | 5 | 1 | 50 |
| 1.67 | 1.67 | 3 | 50 |
| 1 | 1 | 5 | 50 |
| 0.625 | 0.625 | 8 | 50 |
| 0.5 | 0.5 | 10 | 50 |
| 10 | 10 | 0.5 | 25 |
| 5 | 5 | 1 | 25 |
| 1.67 | 1.67 | 3 | 25 |
| 1 | 1 | 5 | 25 |
| 0.625 | 0.625 | 8 | 25 |
| 0.5 | 0.5 | 10 | 25 |

Telescoped Reaction in Tube:
Nitrosation Reagent: $NaNO_2/HCO_2H$, 4

| R1 1 + Triethyl amine µL/min | R2 2 µL/min | Reactor volume, cm | Step 1 | Extraction step, $H_2O$ µL/min | Extraction step, DCM µL/min | R3 $NaNO_2$ µL/min | R3 $HCO_2H$ µL/min | Step 2 |
|---|---|---|---|---|---|---|---|---|
| 12.56 | 12.56 | Step 1: 5 Step 2: 100 | 1 min, 50° C. | 50.24 | 25.12 | 25.12 | 25.12 | 5 min, 0° C. |
| 12.56 | 12.56 | Step 1: 10 Step 2: 100 | 2 min, 50° C. | 50.24 | 25.12 | 25.12 | 25.12 | 5 min, 0° C. |
| 12.56 | 12.56 | Step 1: 50 Step 2: 100 | 10 min, 50° C. | 50.24 | 25.12 | 25.12 | 25.12 | 5 min, 0° C. |
| 12.56 | 12.56 | Step 1: 50 Step 2: 100 | 10 min, 50° C. | 50.24 | 25.12 | 50.24 | 67.02 | 3 min, 0° C. |

Nitrosation Reagent: TBN, 5
Reactor volume: Step 1=5 cm; Step 2=100 cm

| R1 1 + Triethyl amine µL/min | R2 2 µL/min | Step 1 | Extraction step, $H_2O$ µL/min | Extraction step, DCM µL/min | R3 TBN µL/min | Step 2 |
|---|---|---|---|---|---|---|
| 12.56 | 12.56 | 1 min, 50° C. | 50.24 | 25.12 | 50.2 | 5 min, 25/50° C. |
| 12.56 | 12.56 | 1 min, 50° C. | 50.24 | 25.12 | 12.56 | 8 min, 25° C. |

| DESI-MS data of the nitrosation reaction using 4 in different stoichiometries ||||||||||
|---|---|---|---|---|---|---|---|---|---|
| Starting Material | Starting Material | Solvent | Stoichiometry | Product m/z | Intensity (Average) | Stdev | Intensity (max) | Normalized Intensity (Average) | Normalized Stdev | Normalized Intensity (max) | no of spots, n |
| 3 | 4 | Acetonitrile | 150 | 169.2 | 213.3 | 191.6 | 934.1 | 0.025 | 0.030 | 0.166 | 144 |
| 3 | 4 | Acetonitrile | 150 | 234.7 | 8.0 | 6.7 | 45.1 | 0.001 | 0.001 | 0.007 | 144 |
| 3 | 4 | Acetonitrile | 150 | 239.4 | 1206.9 | 1349.7 | 6575.7 | 0.069 | 0.066 | 0.284 | 144 |
| 3 | 4 | Acetonitrile | 150 | 241.0 | 390.4 | 412.9 | 1980.9 | 0.022 | 0.020 | 0.088 | 144 |
| 3 | 4 | Acetonitrile | 150 | 250.4 | 143.7 | 184.3 | 923.0 | 0.008 | 0.005 | 0.024 | 144 |
| 3 | 4 | Acetonitrile | 150 | 251.2 | 34.7 | 40.6 | 205.3 | 0.002 | 0.001 | 0.006 | 144 |
| 3 | 4 | Acetonitrile | 150 | 337.4 | 831.0 | 707.6 | 4214.5 | 0.043 | 0.016 | 0.100 | 144 |
| 3 | 4 | Acetonitrile | 150 | 373.4 | 195.1 | 203.4 | 1017.1 | 0.010 | 0.006 | 0.026 | 144 |
| 3 | 4 | Acetonitrile | 100 | 169.2 | 428.3 | 487.1 | 3538.6 | 0.021 | 0.019 | 0.124 | 144 |
| 3 | 4 | Acetonitrile | 100 | 234.7 | 19.3 | 15.1 | 80.5 | 0.002 | 0.002 | 0.008 | 144 |
| 3 | 4 | Acetonitrile | 100 | 239.4 | 2066.8 | 2519.0 | 12435.6 | 0.061 | 0.049 | 0.220 | 144 |
| 3 | 4 | Acetonitrile | 100 | 241.0 | 664.8 | 776.1 | 3676.1 | 0.020 | 0.015 | 0.070 | 144 |
| 3 | 4 | Acetonitrile | 100 | 250.4 | 179.0 | 200.3 | 1072.1 | 0.006 | 0.003 | 0.016 | 144 |
| 3 | 4 | Acetonitrile | 100 | 251.2 | 50.4 | 57.4 | 348.6 | 0.002 | 0.001 | 0.005 | 144 |
| 3 | 4 | Acetonitrile | 100 | 337.4 | 1541.9 | 1537.4 | 9588.3 | 0.050 | 0.018 | 0.105 | 144 |
| 3 | 4 | Acetonitrile | 100 | 373.4 | 261.3 | 307.9 | 1751.0 | 0.008 | 0.004 | 0.022 | 144 |
| 3 | 4 | Acetonitrile | 50 | 169.2 | 53.9 | 58.1 | 322.0 | 0.018 | 0.019 | 0.105 | 144 |
| 3 | 4 | Acetonitrile | 50 | 234.7 | 11.7 | 16.2 | 177.5 | 0.004 | 0.002 | 0.015 | 144 |
| 3 | 4 | Acetonitrile | 50 | 239.4 | 382.9 | 825.0 | 5452.0 | 0.045 | 0.062 | 0.326 | 144 |
| 3 | 4 | Acetonitrile | 50 | 241.0 | 124.8 | 257.2 | 1692.1 | 0.016 | 0.019 | 0.101 | 144 |
| 3 | 4 | Acetonitrile | 50 | 250.4 | 21.3 | 24.1 | 145.3 | 0.005 | 0.002 | 0.012 | 144 |
| 3 | 4 | Acetonitrile | 50 | 251.2 | 6.3 | 6.7 | 37.3 | 0.001 | 0.001 | 0.004 | 144 |
| 3 | 4 | Acetonitrile | 50 | 337.4 | 116.2 | 130.7 | 681.0 | 0.020 | 0.015 | 0.075 | 144 |
| 3 | 4 | Acetonitrile | 50 | 373.4 | 21.0 | 24.5 | 133.5 | 0.004 | 0.003 | 0.014 | 144 |
| 3 | 4 | Acetonitrile | 200 | 169.2 | 134.4 | 122.3 | 642.8 | 0.007 | 0.002 | 0.012 | 144 |
| 3 | 4 | Acetonitrile | 200 | 234.7 | 7.7 | 8.7 | 57.9 | 0.001 | 0.001 | 0.003 | 144 |
| 3 | 4 | Acetonitrile | 200 | 239.4 | 2162.9 | 2123.7 | 15812.4 | 0.119 | 0.056 | 0.297 | 144 |
| 3 | 4 | Acetonitrile | 200 | 241.0 | 608.6 | 518.4 | 4106.0 | 0.035 | 0.017 | 0.090 | 144 |
| 3 | 4 | Acetonitrile | 200 | 250.4 | 39.5 | 26.3 | 138.1 | 0.003 | 0.001 | 0.006 | 144 |
| 3 | 4 | Acetonitrile | 200 | 251.2 | 20.5 | 49.7 | 382.9 | 0.001 | 0.000 | 0.002 | 144 |
| 3 | 4 | Acetonitrile | 200 | 337.4 | 485.0 | 296.1 | 1620.7 | 0.028 | 0.007 | 0.042 | 144 |
| 3 | 4 | Acetonitrile | 200 | 373.4 | 73.1 | 51.3 | 324.3 | 0.004 | 0.001 | 0.007 | 144 |
| 3 | 4 | THF | 200 | 169.2 | 1024.5 | 744.7 | 6746.3 | 0.041 | 0.059 | 0.443 | 144 |
| 3 | 4 | THF | 200 | 234.7 | 30.8 | 36.3 | 222.7 | 0.002 | 0.001 | 0.006 | 144 |
| 3 | 4 | THF | 200 | 239.4 | 1067.2 | 1527.8 | 7808.4 | 0.022 | 0.034 | 0.174 | 144 |

-continued

| | | | | | | | | | | |
|---|---|---|---|---|---|---|---|---|---|---|
| 3 | 4 | THF | 200 | 241.0 | 333.9 | 480.7 | 2373.1 | 0.007 | 0.010 | 0.057 | 144 |
| 3 | 4 | THF | 200 | 250.4 | 749.2 | 367.0 | 2331.3 | 0.011 | 0.004 | 0.022 | 144 |
| 3 | 4 | THF | 200 | 251.2 | 237.1 | 227.8 | 1263.0 | 0.003 | 0.002 | 0.009 | 144 |
| 3 | 4 | THF | 200 | 337.4 | 13765.9 | 7680.8 | 50455.2 | 0.186 | 0.054 | 0.343 | 144 |
| 3 | 4 | THF | 200 | 373.4 | 1096.5 | 568.4 | 3314.2 | 0.016 | 0.005 | 0.038 | 144 |
| 3 | 4 | THF | 150 | 169.2 | 680.3 | 705.5 | 3251.7 | 0.036 | 0.033 | 0.202 | 144 |
| 3 | 4 | THF | 150 | 234.7 | 43.2 | 44.1 | 295.0 | 0.003 | 0.001 | 0.009 | 144 |
| 3 | 4 | THF | 150 | 239.4 | 1106.3 | 2107.4 | 12553.7 | 0.021 | 0.031 | 0.143 | 144 |
| 3 | 4 | THF | 150 | 241.0 | 366.5 | 601.2 | 2985.4 | 0.008 | 0.009 | 0.044 | 144 |
| 3 | 4 | THF | 150 | 250.4 | 349.0 | 338.2 | 1672.1 | 0.007 | 0.004 | 0.020 | 144 |
| 3 | 4 | THF | 150 | 251.2 | 92.1 | 92.6 | 353.0 | 0.002 | 0.001 | 0.008 | 144 |
| 3 | 4 | THF | 150 | 337.4 | 2590.0 | 3621.7 | 15618.2 | 0.044 | 0.051 | 0.185 | 144 |
| 3 | 4 | THF | 150 | 373.4 | 291.1 | 374.6 | 1736.1 | 0.006 | 0.006 | 0.024 | 144 |
| 3 | 4 | THF | 100 | 169.2 | 1152.9 | 849.2 | 4316.7 | 0.053 | 0.038 | 0.236 | 144 |
| 3 | 4 | THF | 100 | 234.7 | 40.4 | 42.7 | 243.0 | 0.002 | 0.001 | 0.014 | 144 |
| 3 | 4 | THF | 100 | 239.4 | 486.4 | 1259.8 | 8600.9 | 0.008 | 0.019 | 0.149 | 144 |
| 3 | 4 | THF | 100 | 241.0 | 166.2 | 407.2 | 2879.3 | 0.003 | 0.006 | 0.044 | 144 |
| 3 | 4 | THF | 100 | 250.4 | 1070.5 | 451.4 | 2449.5 | 0.013 | 0.004 | 0.020 | 144 |
| 3 | 4 | THF | 100 | 251.2 | 260.9 | 172.7 | 1492.2 | 0.003 | 0.001 | 0.011 | 144 |
| 3 | 4 | THF | 100 | 337.4 | 14213.4 | 9456.4 | 39713.7 | 0.157 | 0.076 | 0.339 | 144 |
| 3 | 4 | THF | 100 | 373.4 | 1262.2 | 675.0 | 3233.6 | 0.016 | 0.006 | 0.030 | 144 |
| 3 | 4 | THF | 50 | 169.2 | 708.7 | 560.9 | 3726.2 | 0.060 | 0.034 | 0.211 | 144 |
| 3 | 4 | THF | 50 | 234.7 | 46.1 | 56.3 | 341.8 | 0.003 | 0.002 | 0.020 | 144 |
| 3 | 4 | THF | 50 | 239.4 | 91.6 | 164.1 | 938.4 | 0.003 | 0.003 | 0.023 | 144 |
| 3 | 4 | THF | 50 | 241.0 | 54.0 | 70.6 | 369.5 | 0.003 | 0.003 | 0.015 | 144 |
| 3 | 4 | THF | 50 | 250.4 | 783.5 | 422.1 | 2172.0 | 0.012 | 0.003 | 0.018 | 144 |
| 3 | 4 | THF | 50 | 251.2 | 227.3 | 310.1 | 2172.0 | 0.003 | 0.002 | 0.014 | 144 |
| 3 | 4 | THF | 50 | 337.4 | 10050.7 | 9141.9 | 52775.8 | 0.125 | 0.074 | 0.268 | 144 |
| 3 | 4 | THF | 50 | 373.4 | 911.9 | 744.6 | 4270.9 | 0.012 | 0.006 | 0.022 | 144 |
| Rhodamine | | | | 443.3 | 12213.1 | 8739.2 | 70545.6 | 0.491 | 0.101 | 0.690 | 384 |

DESI-MS data of the nitrosation reaction using 4 as a nitrosation reagent

| Starting Material | Starting Material | Solvent | Product m/z | Intensity (Average) | Stdev | Intensity (max) | Normalized Intensity (Average) | Normalized Stdev | Normalized Intensity (max) | No of spots, n |
|---|---|---|---|---|---|---|---|---|---|---|
| 3 | 4 | Toluene | 169.2 | 2554.4 | 5564.3 | 36332.5 | 0.406 | 0.173 | 0.719 | 144 |
| 3 | 4 | Toluene | 205.7 | 7.2 | 10.4 | 63.4 | 0.003 | 0.003 | 0.015 | 144 |
| 3 | 4 | Toluene | 234.7 | 2.8 | 4.5 | 24.2 | 0.001 | 0.001 | 0.004 | 144 |
| 3 | 4 | Toluene | 239.4 | 2.7 | 5.8 | 38.3 | 0.000 | 0.001 | 0.007 | 144 |
| 3 | 4 | Toluene | 241.0 | 2.5 | 5.8 | 38.1 | 0.000 | 0.001 | 0.004 | 144 |
| 3 | 4 | Toluene | 250.4 | 1.4 | 4.4 | 43.3 | 0.000 | 0.001 | 0.004 | 144 |
| 3 | 4 | Toluene | 251.2 | 30.9 | 134.5 | 1279.6 | 0.002 | 0.006 | 0.039 | 144 |
| 3 | 4 | Toluene | 337.4 | 100.7 | 267.5 | 1413.6 | 0.007 | 0.018 | 0.146 | 144 |
| 3 | 4 | Toluene | 373.4 | 440.4 | 1209.9 | 8746.2 | 0.026 | 0.043 | 0.215 | 144 |
| 3 | 4 | Acetonitrile | 169.2 | 861.8 | 2266.6 | 24796.5 | 0.471 | 0.136 | 0.774 | 144 |
| 3 | 4 | Acetonitrile | 205.7 | 6.4 | 12.7 | 84.5 | 0.003 | 0.004 | 0.026 | 144 |
| 3 | 4 | Acetonitrile | 234.7 | 0.8 | 2.0 | 15.5 | 0.000 | 0.001 | 0.007 | 144 |
| 3 | 4 | Acetonitrile | 239.4 | 1.1 | 2.4 | 17.8 | 0.000 | 0.000 | 0.002 | 144 |
| 3 | 4 | Acetonitrile | 241.0 | 6.9 | 18.6 | 151.1 | 0.001 | 0.002 | 0.008 | 144 |
| 3 | 4 | Acetonitrile | 250.4 | 5.3 | 13.5 | 106.8 | 0.001 | 0.002 | 0.012 | 144 |
| 3 | 4 | Acetonitrile | 251.2 | 330.2 | 517.7 | 2676.7 | 0.039 | 0.035 | 0.213 | 144 |
| 3 | 4 | Acetonitrile | 337.4 | 46.4 | 73.3 | 493.7 | 0.005 | 0.006 | 0.033 | 144 |
| 3 | 4 | Acetonitrile | 373.4 | 651.5 | 1237.0 | 9488.0 | 0.065 | 0.035 | 0.190 | 144 |
| 3 | 4 | DMSO | 169.2 | 4904.5 | 8789.6 | 53558.7 | 0.355 | 0.137 | 0.642 | 144 |
| 3 | 4 | DMSO | 205.7 | 25.7 | 26.7 | 151.4 | 0.002 | 0.002 | 0.012 | 144 |
| 3 | 4 | DMSO | 234.7 | 1.8 | 2.3 | 13.1 | 0.000 | 0.001 | 0.002 | 144 |
| 3 | 4 | DMSO | 239.4 | 17.1 | 26.6 | 228.2 | 0.001 | 0.000 | 0.002 | 144 |
| 3 | 4 | DMSO | 241.0 | 5.2 | 6.1 | 26.9 | 0.000 | 0.000 | 0.002 | 144 |
| 3 | 4 | DMSO | 250.4 | 1.6 | 9.6 | 110.6 | 0.000 | 0.000 | 0.001 | 144 |
| 3 | 4 | DMSO | 251.2 | 101.2 | 179.2 | 1054.9 | 0.002 | 0.003 | 0.021 | 144 |
| 3 | 4 | DMSO | 337.4 | 443.8 | 791.7 | 4937.7 | 0.009 | 0.011 | 0.053 | 144 |
| 3 | 4 | DMSO | 373.4 | 2602.8 | 3506.2 | 30323.8 | 0.049 | 0.033 | 0.232 | 144 |
| 3 | 4 | THF | 169.2 | 1604.6 | 1828.4 | 9837.0 | 0.343 | 0.165 | 0.671 | 144 |
| 3 | 4 | THF | 205.7 | 14.3 | 16.2 | 107.3 | 0.002 | 0.003 | 0.014 | 144 |
| 3 | 4 | THF | 234.7 | 9.2 | 20.8 | 141.7 | 0.000 | 0.001 | 0.003 | 144 |
| 3 | 4 | THF | 239.4 | 68.5 | 72.4 | 381.6 | 0.002 | 0.002 | 0.007 | 144 |
| 3 | 4 | THF | 241.0 | 22.7 | 22.2 | 99.5 | 0.001 | 0.000 | 0.004 | 144 |
| 3 | 4 | THF | 250.4 | 4.1 | 7.3 | 32.2 | 0.000 | 0.000 | 0.001 | 144 |
| 3 | 4 | THF | 251.2 | 254.1 | 351.0 | 1963.4 | 0.008 | 0.008 | 0.040 | 144 |
| 3 | 4 | THF | 337.4 | 122.6 | 116.9 | 840.1 | 0.003 | 0.002 | 0.019 | 144 |
| 3 | 4 | THF | 373.4 | 3643.6 | 3629.0 | 24476.2 | 0.079 | 0.036 | 0.222 | 144 |
| 3 | 4 | Ethanol | 169.2 | 1939.9 | 2663.0 | 23988.5 | 0.315 | 0.159 | 0.644 | 144 |
| 3 | 4 | Ethanol | 205.7 | 18.0 | 22.0 | 108.9 | 0.003 | 0.003 | 0.017 | 144 |
| 3 | 4 | Ethanol | 234.7 | 9.7 | 28.9 | 313.9 | 0.001 | 0.001 | 0.003 | 144 |
| 3 | 4 | Ethanol | 239.4 | 3.1 | 3.4 | 20.9 | 0.000 | 0.000 | 0.002 | 144 |
| 3 | 4 | Ethanol | 241.0 | 4.1 | 3.4 | 17.3 | 0.000 | 0.000 | 0.003 | 144 |
| 3 | 4 | Ethanol | 250.4 | 3.5 | 3.4 | 17.0 | 0.000 | 0.000 | 0.002 | 144 |

-continued

| | | | | | | | | | |
|---|---|---|---|---|---|---|---|---|---|
| 3 | 4 | Ethanol | 251.2 | 53.0 | 37.6 | 152.7 | 0.002 | 0.001 | 0.006 | 144 |
| 3 | 4 | Ethanol | 337.4 | 263.7 | 193.3 | 1112.6 | 0.009 | 0.005 | 0.049 | 144 |
| 3 | 4 | Ethanol | 373.4 | 553.9 | 508.5 | 2842.8 | 0.024 | 0.010 | 0.074 | 144 |
| 3 | 4 | DCM | 169.2 | 463.4 | 643.7 | 3574.7 | 0.429 | 0.135 | 0.733 | 144 |
| 3 | 4 | DCM | 205.7 | 6.8 | 10.5 | 72.0 | 0.005 | 0.008 | 0.056 | 144 |
| 3 | 4 | DCM | 234.7 | 1.8 | 9.0 | 77.5 | 0.000 | 0.001 | 0.006 | 144 |
| 3 | 4 | DCM | 239.4 | 1.6 | 3.8 | 22.9 | 0.000 | 0.001 | 0.005 | 144 |
| 3 | 4 | DCM | 241.0 | 6.9 | 17.3 | 111.6 | 0.001 | 0.003 | 0.027 | 144 |
| 3 | 4 | DCM | 250.4 | 4.4 | 11.7 | 91.1 | 0.001 | 0.002 | 0.009 | 144 |
| 3 | 4 | DCM | 251.2 | 68.1 | 211.5 | 1683.3 | 0.009 | 0.014 | 0.103 | 144 |
| 3 | 4 | DCM | 337.4 | 32.4 | 77.4 | 572.0 | 0.007 | 0.013 | 0.060 | 144 |
| 3 | 4 | DCM | 373.4 | 381.0 | 586.2 | 3159.2 | 0.072 | 0.062 | 0.206 | 144 |
| 3 | 4 | Ethyl Acetate | 169.2 | 2710.5 | 3037.9 | 15437.7 | 0.325 | 0.124 | 0.586 | 144 |
| 3 | 4 | Ethyl Acetate | 205.7 | 23.4 | 33.0 | 173.7 | 0.005 | 0.006 | 0.042 | 144 |
| 3 | 4 | Ethyl Acetate | 234.7 | 7.6 | 29.1 | 260.3 | 0.001 | 0.002 | 0.017 | 144 |
| 3 | 4 | Ethyl Acetate | 239.4 | 2.0 | 3.6 | 16.7 | 0.000 | 0.000 | 0.002 | 144 |
| 3 | 4 | Ethyl Acetate | 241.0 | 4.7 | 9.6 | 73.9 | 0.000 | 0.000 | 0.002 | 144 |
| 3 | 4 | Ethyl Acetate | 250.4 | 3.5 | 7.4 | 58.3 | 0.000 | 0.000 | 0.002 | 144 |
| 3 | 4 | Ethyl Acetate | 251.2 | 115.4 | 304.2 | 2298.6 | 0.005 | 0.009 | 0.058 | 144 |
| 3 | 4 | Ethyl Acetate | 337.4 | 34.3 | 65.0 | 512.9 | 0.002 | 0.002 | 0.012 | 144 |
| 3 | 4 | Ethyl Acetate | 373.4 | 2627.7 | 3123.4 | 13965.7 | 0.104 | 0.081 | 0.247 | 144 |
| 3 | 4 | Methanol | 169.2 | 1516.5 | 3046.6 | 34891.7 | 0.369 | 0.172 | 0.780 | 144 |
| 3 | 4 | Methanol | 205.7 | 15.8 | 21.8 | 167.1 | 0.003 | 0.004 | 0.028 | 144 |
| 3 | 4 | Methanol | 234.7 | 1.3 | 1.6 | 7.2 | 0.000 | 0.001 | 0.002 | 144 |
| 3 | 4 | Methanol | 239.4 | 1.6 | 2.1 | 15.3 | 0.000 | 0.000 | 0.002 | 144 |
| 3 | 4 | Methanol | 241.0 | 2.7 | 4.0 | 22.3 | 0.000 | 0.000 | 0.002 | 144 |
| 3 | 4 | Methanol | 250.4 | 1.3 | 2.3 | 14.7 | 0.000 | 0.000 | 0.002 | 144 |
| 3 | 4 | Methanol | 251.2 | 19.6 | 25.3 | 173.7 | 0.001 | 0.001 | 0.006 | 144 |
| 3 | 4 | Methanol | 337.4 | 288.8 | 315.4 | 1590.6 | 0.013 | 0.010 | 0.052 | 144 |
| 3 | 4 | Methanol | 373.4 | 510.8 | 507.8 | 2698.7 | 0.027 | 0.014 | 0.072 | 144 |
| 3 | | | 443.3 | 12333.9 | 13328.7 | 384.0 | 0.354 | 0.083 | 0.646 | 384 |
| 3 | 5 | Ethyl Acetate | 169.2 | 41.1 | 47.5 | 326.1 | 0.006 | 0.005 | 0.028 | 144 |
| 3 | 5 | Ethyl Acetate | 205.7 | 26.2 | 10.1 | 59.8 | 0.004 | 0.001 | 0.011 | 144 |
| 3 | 5 | Ethyl Acetate | 234.7 | 46.6 | 22.4 | 225.0 | 0.007 | 0.002 | 0.026 | 144 |
| 3 | 5 | Ethyl Acetate | 239.4 | 54.1 | 121.6 | 768.5 | 0.005 | 0.006 | 0.027 | 144 |
| 3 | 5 | Ethyl Acetate | 241.0 | 18.6 | 34.1 | 215.5 | 0.002 | 0.002 | 0.010 | 144 |
| 3 | 5 | Ethyl Acetate | 250.4 | 243.1 | 89.4 | 605.5 | 0.038 | 0.008 | 0.076 | 144 |
| 3 | 5 | Ethyl Acetate | 251.2 | 239.7 | 89.6 | 605.5 | 0.039 | 0.010 | 0.112 | 144 |
| 3 | 5 | Ethyl Acetate | 337.4 | 6.5 | 4.5 | 38.0 | 0.001 | 0.001 | 0.004 | 144 |
| 3 | 5 | Ethyl Acetate | 373.4 | 19.5 | 23.7 | 107.1 | 0.003 | 0.004 | 0.022 | 144 |
| 3 | 5 | Ethanol | 169.2 | 1059.5 | 1113.0 | 5710.9 | 0.047 | 0.027 | 0.128 | 144 |
| 3 | 5 | Ethanol | 205.7 | 44.2 | 47.6 | 224.7 | 0.002 | 0.001 | 0.006 | 144 |
| 3 | 5 | Ethanol | 234.7 | 22.5 | 14.2 | 73.3 | 0.001 | 0.000 | 0.002 | 144 |
| 3 | 5 | Ethanol | 239.4 | 437.1 | 485.3 | 2453.7 | 0.016 | 0.012 | 0.091 | 144 |
| 3 | 5 | Ethanol | 241.0 | 155.0 | 199.6 | 1496.5 | 0.005 | 0.004 | 0.027 | 144 |
| 3 | 5 | Ethanol | 250.4 | 75.4 | 57.5 | 339.3 | 0.003 | 0.002 | 0.009 | 144 |
| 3 | 5 | Ethanol | 251.2 | 33.5 | 21.6 | 123.8 | 0.001 | 0.000 | 0.003 | 144 |
| 3 | 5 | Ethanol | 337.4 | 28.4 | 16.3 | 85.8 | 0.001 | 0.000 | 0.003 | 144 |
| 3 | 5 | Ethanol | 373.4 | 547.1 | 727.2 | 4628.6 | 0.021 | 0.014 | 0.065 | 144 |
| 3 | 5 | THF | 169.2 | 77.4 | 147.1 | 824.4 | 0.008 | 0.009 | 0.066 | 144 |
| 3 | 5 | THF | 205.7 | 23.6 | 18.8 | 81.5 | 0.004 | 0.002 | 0.009 | 144 |
| 3 | 5 | THF | 234.7 | 55.6 | 74.9 | 771.9 | 0.008 | 0.004 | 0.020 | 144 |
| 3 | 5 | THF | 239.4 | 98.5 | 215.8 | 1279.6 | 0.008 | 0.010 | 0.046 | 144 |
| 3 | 5 | THF | 241.0 | 31.2 | 63.7 | 401.6 | 0.002 | 0.003 | 0.013 | 144 |
| 3 | 5 | THF | 250.4 | 278.7 | 221.3 | 1061.8 | 0.046 | 0.021 | 0.088 | 144 |
| 3 | 5 | THF | 251.2 | 285.5 | 222.9 | 1061.8 | 0.048 | 0.020 | 0.088 | 144 |
| 3 | 5 | THF | 337.4 | 5.7 | 5.9 | 46.3 | 0.001 | 0.001 | 0.007 | 144 |
| 3 | 5 | THF | 373.4 | 23.1 | 41.3 | 258.5 | 0.003 | 0.004 | 0.021 | 144 |
| 3 | 5 | DCM | 169.2 | 357.7 | 408.6 | 2428.0 | 0.028 | 0.018 | 0.076 | 144 |
| 3 | 5 | DCM | 205.7 | 56.1 | 22.9 | 159.1 | 0.005 | 0.002 | 0.011 | 144 |
| 3 | 5 | DCM | 234.7 | 111.7 | 69.4 | 561.9 | 0.010 | 0.003 | 0.017 | 144 |
| 3 | 5 | DCM | 239.4 | 255.9 | 372.5 | 1692.9 | 0.019 | 0.016 | 0.055 | 144 |
| 3 | 5 | DCM | 241.0 | 76.3 | 115.2 | 670.7 | 0.006 | 0.005 | 0.018 | 144 |
| 3 | 5 | DCM | 250.4 | 538.9 | 212.4 | 1632.1 | 0.057 | 0.017 | 0.086 | 144 |
| 3 | 5 | DCM | 251.2 | 551.4 | 202.1 | 1632.1 | 0.058 | 0.015 | 0.086 | 144 |
| 3 | 5 | DCM | 337.4 | 3.3 | 3.5 | 28.0 | 0.000 | 0.000 | 0.002 | 144 |
| 3 | 5 | DCM | 373.4 | 102.8 | 212.9 | 2118.2 | 0.007 | 0.007 | 0.038 | 144 |
| 3 | 5 | Toluene | 169.2 | 292.1 | 271.9 | 1570.8 | 0.025 | 0.016 | 0.098 | 144 |
| 3 | 5 | Toluene | 205.7 | 25.0 | 15.0 | 107.4 | 0.003 | 0.001 | 0.011 | 144 |
| 3 | 5 | Toluene | 234.7 | 37.9 | 32.5 | 268.9 | 0.005 | 0.001 | 0.012 | 144 |
| 3 | 5 | Toluene | 239.4 | 179.6 | 173.3 | 1095.6 | 0.012 | 0.007 | 0.034 | 144 |
| 3 | 5 | Toluene | 241.0 | 57.9 | 59.1 | 394.2 | 0.004 | 0.002 | 0.011 | 144 |
| 3 | 5 | Toluene | 250.4 | 257.8 | 80.3 | 515.9 | 0.040 | 0.006 | 0.054 | 144 |
| 3 | 5 | Toluene | 251.2 | 257.5 | 78.3 | 463.2 | 0.040 | 0.006 | 0.054 | 144 |
| 3 | 5 | Toluene | 337.4 | 5.5 | 4.5 | 24.3 | 0.001 | 0.000 | 0.002 | 144 |
| 3 | 5 | Toluene | 373.4 | 136.8 | 119.1 | 632.3 | 0.012 | 0.008 | 0.045 | 144 |
| 3 | 5 | DMSO | 169.2 | 3063.0 | 4126.1 | 20263.6 | 0.192 | 0.113 | 0.754 | 144 |
| 3 | 5 | DMSO | 205.7 | 28.5 | 52.8 | 347.2 | 0.003 | 0.002 | 0.014 | 144 |
| 3 | 5 | DMSO | 234.7 | 19.5 | 14.6 | 117.7 | 0.004 | 0.003 | 0.033 | 144 |

| | | | | | | | | | | |
|---|---|---|---|---|---|---|---|---|---|---|
| 3 | 5 | DMSO | 239.4 | 30.2 | 77.6 | 745.0 | 0.002 | 0.003 | 0.016 | 144 |
| 3 | 5 | DMSO | 241.0 | 10.1 | 24.1 | 233.9 | 0.001 | 0.001 | 0.005 | 144 |
| 3 | 5 | DMSO | 250.4 | 108.8 | 94.5 | 872.6 | 0.020 | 0.008 | 0.039 | 144 |
| 3 | 5 | DMSO | 251.2 | 105.8 | 71.3 | 325.7 | 0.022 | 0.007 | 0.040 | 144 |
| 3 | 5 | DMSO | 337.4 | 5.5 | 8.9 | 57.0 | 0.001 | 0.001 | 0.007 | 144 |
| 3 | 5 | DMSO | 373.4 | 2038.4 | 3628.2 | 27327.2 | 0.095 | 0.060 | 0.239 | 144 |
| 3 | 5 | Methanol | 169.2 | 1526.0 | 1662.0 | 6465.5 | 0.070 | 0.055 | 0.179 | 144 |
| 3 | 5 | Methanol | 205.7 | 46.2 | 46.0 | 249.9 | 0.002 | 0.001 | 0.006 | 144 |
| 3 | 5 | Methanol | 234.7 | 24.3 | 25.1 | 113.3 | 0.001 | 0.000 | 0.003 | 144 |
| 3 | 5 | Methanol | 239.4 | 483.9 | 642.3 | 3403.1 | 0.019 | 0.017 | 0.090 | 144 |
| 3 | 5 | Methanol | 241.0 | 194.0 | 382.7 | 3346.8 | 0.006 | 0.006 | 0.029 | 144 |
| 3 | 5 | Methanol | 250.4 | 71.5 | 104.6 | 744.7 | 0.003 | 0.002 | 0.010 | 144 |
| 3 | 5 | Methanol | 251.2 | 43.1 | 65.4 | 548.5 | 0.002 | 0.001 | 0.006 | 144 |
| 3 | 5 | Methanol | 337.4 | 26.3 | 29.5 | 167.7 | 0.001 | 0.001 | 0.004 | 144 |
| 3 | 5 | Methanol | 373.4 | 1043.9 | 1687.0 | 11607.0 | 0.039 | 0.035 | 0.128 | 144 |
| 3 | 5 | Acetonitrile | 169.2 | 3290.0 | 3100.9 | 15073.0 | 0.150 | 0.056 | 0.313 | 144 |
| 3 | 5 | Acetonitrile | 205.7 | 33.4 | 12.5 | 102.0 | 0.004 | 0.001 | 0.008 | 144 |
| 3 | 5 | Acetonitrile | 234.7 | 57.2 | 44.7 | 317.8 | 0.006 | 0.002 | 0.012 | 144 |
| 3 | 5 | Acetonitrile | 239.4 | 187.1 | 221.0 | 1440.7 | 0.008 | 0.004 | 0.025 | 144 |
| 3 | 5 | Acetonitrile | 241.0 | 64.9 | 87.3 | 669.7 | 0.003 | 0.001 | 0.008 | 144 |
| 3 | 5 | Acetonitrile | 250.4 | 299.6 | 100.6 | 629.8 | 0.038 | 0.010 | 0.063 | 144 |
| 3 | 5 | Acetonitrile | 251.2 | 311.5 | 96.9 | 629.8 | 0.040 | 0.009 | 0.063 | 144 |
| 3 | 5 | Acetonitrile | 337.4 | 8.2 | 9.1 | 50.7 | 0.000 | 0.000 | 0.005 | 144 |
| 3 | 5 | Acetonitrile | 373.4 | 1274.8 | 1544.7 | 12113.3 | 0.049 | 0.025 | 0.120 | 144 |
| 3 | | | 443.3 | 40997.0 | 24891.7 | 384.0 | 0.654 | 0.118 | 0.807 | 384 |

REFERENCES

[1] a) T. Chakkath, S. Lavergne, T. M. Fan, D. Bunick, L. Dirikolu, *Vet. Sci.* 2015, 2, 52-68; b) L. Dirikolu, T. Chakkath, T. Fan, N. R. Mente, *J. Anal. Toxicol.* 2009, 33, 595-603.

[2] J. W. Lown, S. M. S. Chauhan, *J. Org. Chem.* 1981, 46, 5309-5321.

[3] B. Kaina, M. Christmann, S. Naumann, W. P. Roos, *DNA Repair* 2007, 6, 1079-1099.

[4] F. Y. Lee, P. Workman, J. T. Roberts, N. M. Bleehen, *Cancer Chemother. Pharmacol.* 1985, 14, 125-131.

[5] J. Funaro, H. Friedman, M. Weant, *Cancer Lett.* 2017, 13-14.

[6] a) D. Webb, T. F. Jamison, *Chem. Sci.* 2010, 1, 675-680; b) J. Wegner, S. Ceylan, A. Kirschning, Chem. Commun. 2011, 47, 4583-4592; c) J. I. Yoshida, H. Kim, A. Nagaki, *Chemsuschem* 2011, 4, 331-340; d) J.-i. Yoshida, Y. Takahashi, A. Nagaki, *Chem. Commun.* 2013, 49, 9896-9904; e) V. Hessel, D. Kralisch, N. Kockmann, T. Noel, Q. Wang, *ChemSusChem* 2013, 6, 746-789; f) K. F. Jensen, B. J. Reizman, S. G. Newman, *Lab Chip* 2014, 14, 3206-3212; g) B. Gutmann, D. Cantillo, C. O. Kappe, Angew. *Chem. Int. Ed.* 2015, 54, 6688-6728; h) D. Cambié, C. Bottecchia, N. J. W. Straathof, V. Hessel, T. Noël, *Chem. Rev.* 2016, 116, 10276-10341; i) J. S. Poh, S. Makai, T. von Keutz, D. N. Tran, C. Battilocchio, P. Pasau, S. V. Ley, *Angew. Chem. Int. Ed.* 2017, 56, 1864-1868; j) Z. Yu, X. Ye, Q. Xu, X. Xie, H. Dong, W. Su, *Org. Process Res. Dev.* 2017, 21, 1644-1652; k) J. Britton, C. L. Raston, *Chem. Soc. Rev.* 2017, 46, 1250-1271;1) M. Berton, L. Huck, J. Alcázar, *Nat. Protoc.* 2018, 13, 324.

[7] a) H. V., *Chem. Eng. Technol.* 2009, 32, 1655-1681; b) N. Zaborenko, M. W. Bedore, T. F. Jamison, K. F. Jensen, *Org. Process Res. Dev.* 2011, 15, 131-139; c) C. Wiles, P. Watts, *Chem. Commun.* 2011, 47, 6512-6535; d) J. Wegner, S. Ceylan, A. Kirschning, *Adv. Synth. Catal.* 2012, 354, 17-57; e) D. R. Snead, T. F. Jamison, *Chem. Sci.* 2013, 4, 2822-2827; f) C. Len, S. Bruniaux, F. Delbecq, V. Parmar, *Catalysts* 2017, 7, 146; g) L. J. A. M., M. P. D., B. R. L., J. T. F., *Chem. Rec.* 2017, 17, 667-680.

[8] P. D. Morse, T. F. Jamison, *Angew. Chem. Int. Ed.* 2017, 56, 13999-14002.

[9] a) T. Gustafsson, F. Ponten, P. H. Seeberger, *Chem. Commun.* 2008, 1100-1102; b) M. D. Hopkin, I. R. Baxendale, S. V. Ley,*Org. Biomol. Chem.* 2013, 11, 1822-1839; c) B. J. Deadman, M. D. Hopkin, I. R. Baxendale, S. V. Ley, *Org. Biomol. Chem.* 2013, 11, 1766-1800; d) P. R. D. Murray, D. L. Browne, J. C. Pastre, C. Butters, D. Guthrie, S. V. Ley, *Org. Process Res. Dev.* 2013, 17, 1192-1208; e) P. Zhang, M. G. Russell, T. F. Jamison, *Org. Process Res. Dev.* 2014, 18, 1567-1570; f) D. R. Snead, T. F. Jamison, *Angew. Chem. Int. Ed.* 2015, 54, 983-987; g) A. Adamo, R. L. Beingessner, M. Behnam, J. Chen, T. F. Jamison, K. F. Jensen, J. C. Monbaliu, A. S. Myerson, E. M. Revalor, D. R. Snead, T. Stelzer, N. Weeranoppanant, S. Y. Wong, P. Zhang, *Science* 2016, 352, 61-67; h) H. Lin, C. Dai, T. F. Jamison, K. F. Jensen, *Angew. Chem. Int. Ed.* 2017, 56, 8870-8873; i) P. Zhang, N. Weeranoppanant, D. A. Thomas, K. Tahara, T. Stelzer, M. G. Russell, M. O'Mahony, A. S. Myerson, H. Lin, L. P. Kelly, K. F. Jensen, T. F. Jamison, C. Dai, Y. Cui, N. Briggs, R. L. Beingessner, A. Adamo, *Chem. Eur. J.* 2018, 24, 2776-2784; j) C. E. Falcone, Z. Jaman, M. Wleklinski, A. Koswara, D. H. Thompson, R. G. Cooks, *Analyst* 2017, 142, 2836-2845; k) B. P. Loren, M. Wleklinski, A. Koswara, K. Yammine, Y. Hu, Z. K. Nagy, D. H. Thompson, R. G. Cooks, *Chem. Sci.* 2017, 8, 4363-4370; 1) M. Wleklinski, C. E. Falcone, B. P. Loren, Z. Jaman, K. Iyer, H. S. Ewan, S.-H. Hyun, D. H. Thompson, R. G. Cooks, Eur. *J. Org. Chem.* 2016, 2016, 5480-5484; m) H. S. Ewan, K. Iyer, S.-H. Hyun, M. Wleklinski, R. G. Cooks, D. H. Thompson, *Org. Process Res. Dev.* 2017, 21, 1566-1570.

[10] a) R. Elena, R. Anna, G. Stefania, P. Daniele, M. Marisa, *Chem. Eur. J.* 2011, 17, 6221-6226; b) B. Ahmed-Omer, A. J. Sanderson, *Org. Biomol. Chem.* 2011, 9, 3854-3862.

[11] a) S. Newton, C. F. Carter, C. M. Pearson, L. D. Alves, H. Lange, P. Thansandote, S. V. Ley, *Angew. Chem. Int. Ed.* 2014, 53, 4915-4920; b) P. Ludmila, D.

S. B. Joao, H. Zsofia, B. Florine, C. Florian, L. Andrew, Angew. *Chem. Int. Ed.* 2016, 55, 13576-13579.

[12] B. Make, M. J. M., S. Simon, R. J. H., H. A. B., *Chem. Eur. J.* 2010, 16, 11471-11480.

[13] a) K. F. Jensen, *MRS Bull.* 2006, 31, 101-107; b) K. Geyer, T. Gustafsson, P. H. Seeberger, *Synlett* 2009, 2382-2391; c) H. Kim, K. I. Min, K. Inoue, D. J. Im, D. P. Kim, J. Yoshida, *Science* 2016, 352, 691-694; d) K. Troshin, J. F. Hartwig, *Science* 2017, 357, 175-181; e) M. Wleklinski, B. P. Loren, C. R. Ferreira, Z. Jaman, L. Avramova, T. J. P. Sobreira, D. H. Thompson, R. G. Cooks, *Chem. Sci.* 2018, 9, 1647-1653; f) Z. Jaman, A. Mufti, S. Sah, L. Avramova, D. H. Thompson, *Chem. Eur. J.* 2018, 24, 9546-9554.

[14] a) Y. Xin, B. R. M., C. R. Graham, *Angew. Chem. Int. Ed.* 2016, 55, 12960-12972; b) D. R. Ifa, N. E. Manicke, A. L. Dill, R. G. Cooks, *Science* 2008, 321, 805-805.

[15] a) E. S. Freeman, *J. Phys. Chem.* 1956, 60, 1487-1493; b) J. B. Fox, F. B. Suhre, *CRC Cr. Rev. Anal. Chem* 1985, 15 (3), 283

[16] a) T. P. Johnston, G. S. McCaleb, J. A. Montgomery, *J. Med. Chem.* 1975, 18, 104-106; b)B. Ileana, N.-D. I., *J. Prakt. Chem.* 1985, 327, 675-681.

The invention claimed is:

1. A method of producing Lomustine with a continuous flow condition, wherein said Lomustine is prepared using starting materials including cyclohexanamine, 1-chloro-2-isocyanatoethane, triethylamine (TEA), and optionally a solvent via a linear sequence of two chemical reactions performed separately in two telescoped flow reactors, wherein an extractor is coupled with the first telescoping reactor to remove excess starting materials from the first reaction reactor, wherein the second chemical reaction includes the step of nitrosation of an intermediate product, from the first chemical reaction, 1-(2-chloroethyl)-3-cyclohexylurea, using a nitrosation agent, wherein the nitrosation agent is sodium nitrite in formic acid or tert-butyl nitrite.

2. The method of claim 1, further comprising screening the first reaction conditions according to the method of claim 1:

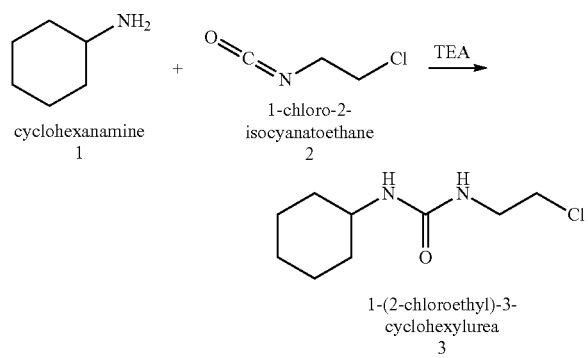

in a continuous flow as a function of temperature, solvent and stoichiometry, wherein the reaction is monitored by thin-layer chromatography (TLC) and mass spectrometry (MS) using a triple quadrupole mass spectrometer operating in positive ion mode to identify an optimum reaction condition for the first reaction.

3. The method of claim 1, comprising sequential)y:
mixing cyclohex anamine (1) and 1-chloro-2-isocyanatoethane (2) with triethylamine (TEA) in the first telescoping reactor at 50° C., for about 1 minute to form the first chemical reaction; wherein an intermediate product 1-(2-chloroethyl)-3-cyclohexylurea (3) is formed in the first chemical reaction;
coupling the extractor with the first telescoping reactor to remove excess base TEA from the first chemical reaction; wherein the extractor is a liquid-liquid extractor;
transferring the intermediate product 1-(2-chloroethyl)-3-cyclohexylurea (3) from the first telescoping reactor to the second telescoping reactor in a continuous flow; and
carrying out nitrosation of the intermediate product 1-(2-chloroethyl)-3-cyclohexylurea (3) in the second telescoping reactor at 25° C. for about 8 minutes using tort-butyl nitrite (tBuONO (5) as the nitrosation agent to form the second chemical reaction; wherein the final product Lomustine is formed in the second chemical reaction.

4. The method of claim 1, wherein the first chemical reaction is performed at a temperature within the range of about 25° C. to about 65° C.

5. The method of claim 1, wherein the first chemical reaction is performed at a temperature selected from the group consisting of room temperature, about 25° C., about 50° C., and about 65° C.

6. The method of claim 1, wherein the first chemical reaction is perfomed for a residence time within the range of about 10 seconds to about three minutes.

7. The method of claim 1, wherein the first chemical reaction is. performed for a residence time selected from the group consisting of about 10 seconds, about 30 seconds, about 60 seconds, and about 180 seconds.

8. The method of claim 1, wherein the extractor is coupled with the first telescoping, reactor to remove excess triethylamine (TEA) from the first reaction.

9. The method of claim 8, wherein the extractor is a liquid-liquid extractor.

10. The method of claim 1, wherein the nitrosation is carried out at a temperature of about 0° C. when sodium nitrite in formic acid is used as the nitrosation agent or about 25° C. to about 50° C. when tent-butyl nitrite is used as the nitrosation agent.

11. The method of claim 1, wherein the second chemical reaction is performed in a solvent Selected from the pup consisting of dimethyl sulfoxide (DMSO), toluene, acetonitrile (ACN), dichloromethane (DCM), ethanol (EtOH), and methanol (MeOH).

12. The method of claim 1, wherein the second chemical reaction is performed for a residence time within the range of about 30 seconds to about ten minutes.

13. The method of claim 1, wherein the nitrosation agent is sodium nitrite in formic acid.

14. The method of claim 1, wherein the nitrosation agent is tert-butyl nitrite.

15. The method of claim 13, wherein the second chemical reaction is performed in a solvent selected from the group consisting of ethyl acetate (EtOAc), tetrahydrofuran (THF), dimethyl sulfoxide (DMSO), toluene, acetonitrile (ACN), dichloromethane (DCM), ethanol (DOH), methanol (MeOH), and methanol:water (4:1 v/v).

16. The method of claim 14, wherein the second chemical reaction is performed in a solvent selected from the group consisting of dimethyl sulfoxide (DMSO), toluene, acetonitrile (ACN), dichloromethane (DCM), ethanol (EtOH), methanol (MeOH), and acetonitrile:ethanol (3.7:1 v/v).

17. The method of claim 13, wherein the second chemical reaction is performed at 0° C.

18. The method of claim 1, wherein the two chemical reactions do not include a purification step of a reaction intermediate.

19. The method of claim 1. wherein the first chemical reaction is performed in a solvent selected from the group consisting of ethanol (EtOH). acetonitrile (CCN), Toluene, Ether and tetrahydrofuran (THF).

20. The method of claim 14, wherein the second chemical reaction is performed at a temperature within the range of about 25° C. to about 50° C.

* * * * *